(12) United States Patent
Labarbe et al.

(10) Patent No.: US 11,559,702 B2
(45) Date of Patent: Jan. 24, 2023

(54) CHARGED PARTICLE TREATMENT PLANNING SYSTEM WITH PBS BEAMLETS SEQUENCE OPTIMIZED FOR HIGH DOSE DEPOSITION RATE

(71) Applicant: Ion Beam Applications S.A., Louvain-la-Neuve (BE)

(72) Inventors: Rudi Labarbe, Louvain-la-Neuve (BE); Lucian Hotoiu, Louvain-la-Neuve (BE); Arnaud Pin, Louvain-la-Neuve (BE)

(73) Assignee: Ion Beam Applications, Louvain-la-Neuve (BE)

( * ) Notice: Subject to any disclaimer, the term of this patent is extended or adjusted under 35 U.S.C. 154(b) by 43 days.

(21) Appl. No.: 17/362,559

(22) Filed: Jun. 29, 2021

(65) Prior Publication Data
US 2021/0402214 A1 Dec. 30, 2021

(30) Foreign Application Priority Data

Jun. 30, 2020 (EP) .................................... 20183082
Sep. 3, 2020 (EP) .................................... 20194440

(51) Int. Cl.
*A61N 5/10* (2006.01)
(52) U.S. Cl.
CPC ......... *A61N 5/1031* (2013.01); *A61N 5/1042* (2013.01); *A61N 5/1077* (2013.01); *A61N 2005/1087* (2013.01)
(58) Field of Classification Search
None
See application file for complete search history.

(56) References Cited

U.S. PATENT DOCUMENTS 7,977,657 B2 * 7/2011 Flynn ..................... A61N 5/10
  250/492.3
8,129,701 B2 * 3/2012 Al-Sadah ............. A61N 5/1042
  250/493.1

(Continued)

FOREIGN PATENT DOCUMENTS

EP        3 424 560 A1    1/2019
WO   WO 2011/160235 A1   12/2011

(Continued)

OTHER PUBLICATIONS

European Search Report issued in corresponding European Patent Application 20194440.2-1122 dated Feb. 22, 2021.

(Continued)

*Primary Examiner* — Hoon K Song
(74) *Attorney, Agent, or Firm* — Finnegan, Henderson, Farabow, Garrett & Dunner, LLP

(57) ABSTRACT

A treatment planning system for generating a plan for treatment by radiation with charged particles beams applied by pencil beam scanning onto a target tissue comprising tumoral cells is provided. The treatment planning system performs a dose definition stage defining the doses to be deposited within the peripheral surface, a beam definition stage defining positions and dimensions of the beamlets of the PBS during the at least one high rate fraction, the beams definition stage including a dose rate definition stage comprising at least one high rate fraction, and a beamlets scanning sequence stage defining a scanning sequence of irradiation of the beamlets. The beamlets scanning sequence stage optimizes a time sequence of beamlets emission such that at the end of a fraction j, a dose is deposited onto at least a predefined fraction of each specific volume at a mean deposition rate superior or equal to a predefined value.

13 Claims, 8 Drawing Sheets

(56) References Cited

U.S. PATENT DOCUMENTS

| | | | |
|---|---|---|---|
| 2005/0207531 A1 | 9/2005 | Dempsey et al. | |
| 2010/0104068 A1 | 4/2010 | Kilby et al. | |
| 2011/0180731 A1* | 7/2011 | Welsh | A61N 5/103 378/65 |
| 2012/0136194 A1* | 5/2012 | Zhang | A61N 5/103 600/1 |
| 2013/0087721 A1* | 4/2013 | Nishio | A61N 5/1042 703/1 |
| 2021/0077826 A1* | 3/2021 | Inaniwa | A61N 5/1077 |
| 2021/0322788 A1* | 10/2021 | Liu | A61N 5/1045 |

FOREIGN PATENT DOCUMENTS

| | | |
|---|---|---|
| WO | WO 2017/093469 A1 | 6/2017 |
| WO | WO 2019/018813 A1 | 1/2019 |

OTHER PUBLICATIONS

European Search Report issued in corresponding European Patent Application 20183082.5-1122 dated Nov. 11, 2020.
Kehwar T S. Analytical approach to estimate normal tissue complication probability using best fit of normal tissue tolerance doses into the NTCP equation of the linear quadratic model. J Can Res Ther [serial online] 2005 [cited Jun. 25, 2021];1:168-79. Available from: https://www.cancerjournal.net/text.asp?2005/1/3/168/19597.
Bortfeld, T. (1997), An analytical approximation of the Bragg curve for therapeutic proton beams. Med. Phys., 24: 2024-2033. https://doi.org/10.1118/1.598116.

\* cited by examiner

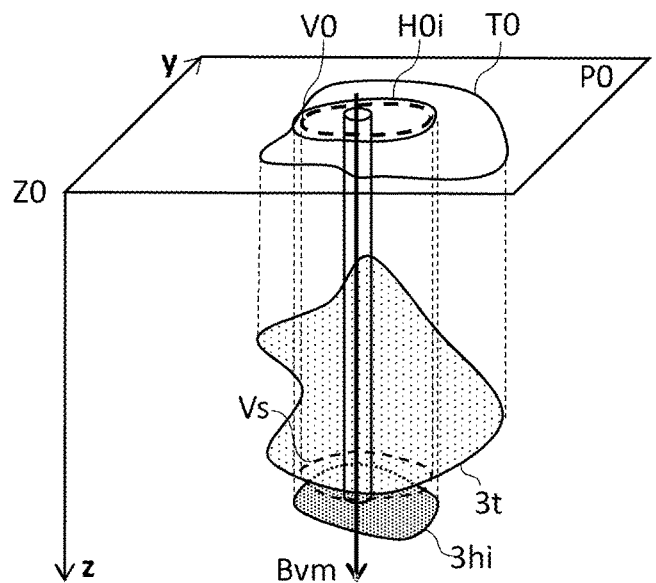
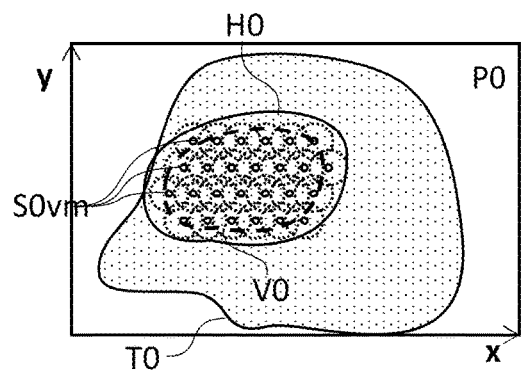
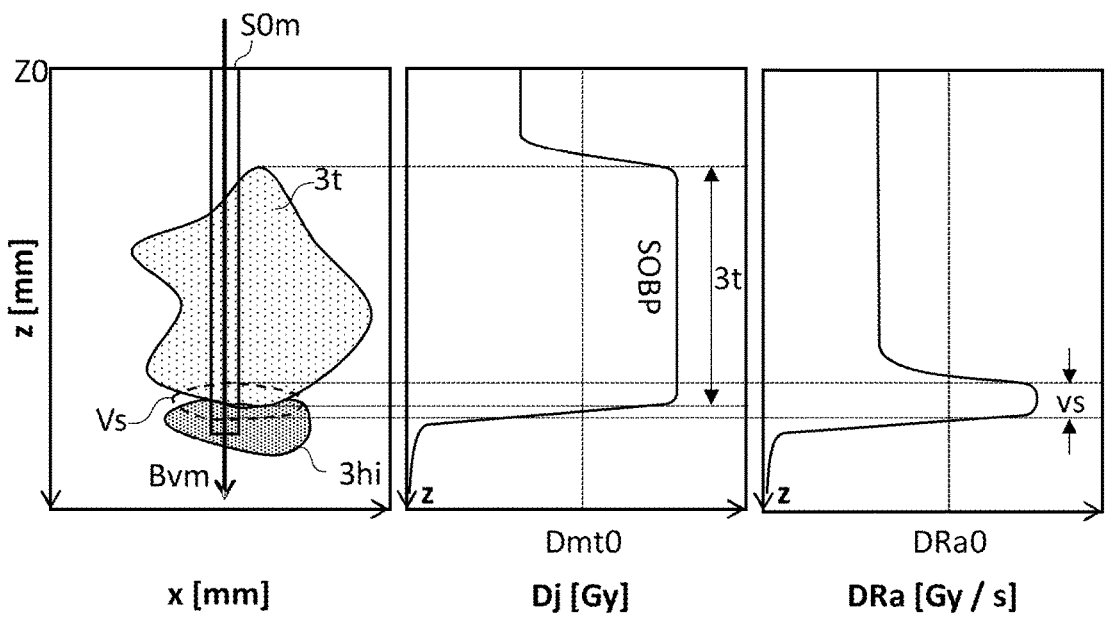
FIG.5(a) FIG.5(b) FIG.5(c) FIG.5(d) FIG.5(e)

CHARGED PARTICLE TREATMENT PLANNING SYSTEM WITH PBS BEAMLETS SEQUENCE OPTIMIZED FOR HIGH DOSE DEPOSITION RATE

CROSS-REFERENCE TO RELATED PATENT APPLICATIONS

This application claims foreign priority of European Patent Application No. 20183082.5, filed Jun. 30, 2020, and European Patent Application No. 20194440.2, filed Sep. 3, 2020, both of which are hereby incorporated by reference.

TECHNICAL FIELD

The present disclosure relates to a treatment planning system (TPS) for generating a plan for treatment with charged particles beams, for instance with proton beams, by pencil beam scanning (PBS) of a target tissue comprising tumoral cells. The plan fulfils predefined clinical criteria for ensuring that at the end of the treatment, the tumoral cells are destroyed or killed, while preserving the healthy cells adjacent to the tumoral cells. The TPS establishes the plan over N irradiation fractions including doses deposited at ultra-high dose deposition rates (HDR) into specific volumes (Vs). The TPS optimizes the scanning sequence of the PBS to ensure that, taking account of the performance of the treatment equipment, doses are deposited at a mean dose deposition rate (DRa) superior or equal to a predefined value (DRa0) of a mean ultra-high dose deposition rate boundary (DRa≥DRa0), into at least a predefined fraction of the volume of each specific volume (Vs).

The plan thus generated ensures an effective treatment of the tumoral cells, with a lower ratio of damages to healthy cells adjacent to the tumoral cells tailored to the particle treatment system used for implementing the treatment plan.

BACKGROUND

Radiation therapy with particles or waves, such as electron beams, protons beams, heavy ions beams, x-rays, γ-rays, and the like, has become a tool for treating patients with tumours.

Pencil beam scanning (PBS) is a technique consisting of steering a beam of charged particles towards a target comprising tumoral cells. PBS reduces unnecessary radiation exposure to surrounding non-cancerous cells by shaping the area being treated to mirror the tumour geometry. Beside the geometry of the target, PBS allows local tuning of the intensity of a beamlets depending on the position of the irradiated cells within the target.

Pencil beam scanning can treat a tumour with a single beam composed of various beamlets or with multiple beams of different orientations each composed of various beamlets, sometimes called intensity modulated proton therapy (IMPT).

Since both tumoral cells and healthy cells are damaged by such radiations, a major challenge in cancer treatment is to define a plan ensuring that the tumoral cells are effectively destroyed or killed, while sparing as much as possible the healthy cells, in particular those adjacent to the tumoral cells. A first step of a treatment plan is the capture of images of the tumoral region by CT-scan. Based on these images, an oncologist identifies the right targets and determines the locations and doses to be deposited to kill the tumoral cells. Such plan must satisfy multiple, often competing, parameters, and is therefore quite complex. For this reason, treatment planning systems are generally computer generated.

A first criterion a treatment plan may fulfil is to ensure that, at the end of the treatment, a total target dose (DmtT) greater than or equal to a minimum target dose (DmtT0) has been delivered to the tumoral cells forming the target effective for destroying/killing the tumoral cells.

A second criterion may be to minimize the degradation of the healthy cells adjacent to the tumoral cells. No matter how accurate the dose deposition, even by PBS, in a volume comprising tumoral cells, a radiation beam reaching the volume comprising the tumoral cells may cross healthy cells and deliver thereto a dose also to healthy cells surrounding or included in that volume. Different radiations deposit their energies in different patterns. For example, X-rays deposit most of their energy near the level of the skin, and the deposited energy decreases with depth. Healthy tissues located upstream of a target volume of tumoral cells therefore receive a higher dose than the tumoral cells of target volume. By contrast, as shown in FIGS. 1(a)&1(c), charged particle beams, in particular protons deposit most of their energy close to the end of their beam path, forming a so-called Bragg peak. By superposing a number of beamlets with their respective Bragg peaks staggered in depth, a sum of individual Bragg Peaks (SOBP) can be defined spanning a whole depth of the volume of tumoral cells or of a fraction of that volume. The healthy cells located upstream of the volume of tumoral cells crossed by a proton beam therefore receive a lower dose than the tumoral cells in the volume. Consequently, proton therapy is well suited for depositing high doses in deep seated tumours.

To minimize the degradation of the healthy cells adjacent to the tumoral cells, the total dose (DhTi) received by a healthy cell may not exceed a maximum allowable dose. As the maximum allowable dose a healthy cell can safely receive in one session may be substantially lower than the minimum target dose (DmtT0) required to destroy the tumoral cells, the total target dose (DmtT) may be delivered to the tumoral cells in one or more fractions (or sessions).

A treatment plan may therefore include the delivery of a predefined total target dose (DmtT) of radiation to all the tumoral cells in N sessions or fractions j, with N≥1, each fraction j delivering a target fraction dose (Dmtj) to a volume of tumoral cells. If N=1, the whole of the predefined total target dose is delivered in a single session. If N>1, the predefined total target dose is delivered in several fractions, possibly to different volumes of tumoral cells, such that at the end of the Nth session, all the tumoral cells have received a cumulated target dose equal to the predefined total target dose (DmtT) required for killing tumoral cells. The number N of fractions depends on the nature of the healthy tissues which determines the maximum fraction dose they can safely receive in a fraction. It also depends on the type of radiation used and on the positions of the healthy cells relative to the tumoral cells, as these parameters at least partially determine the dose deposited on healthy cells crossed by a radiation beam aiming at depositing a target fraction dose (Dmtj) onto a volume containing tumoral cells.

It has been observed that the tumoral cells have a longer recovery time to recover from the damages suffered after an irradiation fraction than healthy cells. This allows a treatment plan to span over several fractions distributed over a period of several days and weeks. By ensuring that the healthy cells receive fraction doses low enough to preserve them, the tumoral cells receive a total target dose cumulated over the N fractions at least equal to the minimum target dose (DmtT), and a recovery time between two successive fractions is sufficient to allow substantial recovery of the healthy cells, but not of the tumoral cells, the treatment plan can ensure that at the end of the treatment, all the tumoral cells have been destroyed, while sparing most healthy cells.

Maximum fraction dose and maximum total dose acceptable to the healthy cells can be defined relative to a Normal Tissue Complication Probability (NTCP) which defines the probability of a given tissue of developing complications upon exposure to a given radiation. Values of boundary doses of radiation yielding a given value of the NTCP for a selection of organs are available in the literature. For example, Kehwar, J. Cancer Res. Ther., September 2005, 1(3), 168, lists in Table 3, on p. 171, a number of doses yielding a 50% NTCP of developing five years after the treatment symptoms as defined in the last column for a number of organs. The volumes 1/3-3/3 in Table 3 indicate the portion of the total volume of the corresponding organ being irradiated. Alternatively, a medical practitioner can have other sources for determining boundary doses, such as personal experience, or referring to other experimental data.

Historically, treatment plans by radiation therapy included the delivery of radiation doses to the treated cells at a conventional dose deposition rate (CDR) lower than 1 Gy/s. With rare exceptions, current radiation therapy facilities deliver dose-rates around 0.1 Gy/s and most clinical protocols involve delivery at regular intervals of N target fraction doses (Dmtj) of 2 to 15 Gy cumulated to reach the total target dose (DmtT) which often exceeds the tolerance limit of normal tissues located in the radiation field, thus damaging them together with the tumoral cells. Recently and as illustrated in FIGS. 2(a) and 2(b), it has been observed that a same dose (D) had different effects on healthy cells but not on tumoral cells when deposited at conventional dose deposition rates (CDR) or at ultra-high dose deposition rate (HDR). HDR can be one or more orders of magnitude larger than conventional dose deposition rates (CDR) usually applied. Deposition of a dose at ultra-high dose deposition rates (HDR) is also referred to as FLASH-radiotherapy (FLASH-RT). It has been observed experimentally on animals and on various organs, that ultra-high rate dose deposition at HDR can significantly spare healthy tissues in comparison with conventional deposition of a same dose at CDR and, at the same time, tumoral cells respond the same or even better to HDR deposition than to CDR deposition. For example, FLASH-RT reportedly elicits in mice a dramatic decrease of the incidence of lung fibrosis, of memory loss subsequent to brain irradiation, and of necrosis of the small intestine while keeping the anti-tumour efficiency unchanged. Such specific normal tissue sparing has been confirmed in large animals and a patient with cutaneous lymphoma has already been treated with FLASH-RT.

As illustrated in FIGS. 3(b) and 3(c), a single beamlet propagating along a beam direction (z) radially deposits doses approximately according to a Gaussian distribution curve, normal to the beam direction (z). In FIG. 3(b), Gaussian deposition curves are illustrated along a direction (x) normal to the beam direction (z). FIG. 3(c) illustrates with shade codes the dose distribution deposited radially by a beamlet. As can be seen in FIGS. 3(b) and 3(c), the beam axes of two adjacent proton beamlets in PBS are distributed according to a spot positions pattern (x, y) and are generally separated from one another by a distance comprised between 1.2 and 2.5 times s, for instance 1.3 to 1.5, wherein $s^2$ is the variance of the Gaussian dose distribution in the spots on the surface plane (Pk) normal to the beam direction (z). It follows that a beamlet (B1) deposits a dose onto an area of the plane (Pk) which impinges over the zone of dose deposition by a second beamlet (B2) adjacent to the first beamlet (B1), yielding the wavy distribution curve illustrated in FIG. 3(b) (two lumps only are illustrated, but this shape becomes more complex with additional adjacent beamlets propagating along the beam direction (z) at a different y-position from the first and second beamlets (B1, B2). Such overlap is essential to ensure a uniform dose deposition of a whole area on the plane (Pk). This has, however, an unexpected effect on the FLASH effect, illustrated in FIG. 3(a). The amplitude of the wavy distribution curve depends inter alia on the distance between two adjacent spots and on the number of spots delivering a dose at a given location.

FIG. 3(a) illustrates the doses deposited as a function of time at a given point on a plane (Pk). It can be seen that at a time (t) of approximately 400 ms a first dose (Di) was deposited by a first beamlet at ultra-high dose rate (DRi) of over 1200 Gy/s, well within FLASH-RT effect. The same point, however received doses (D1, D2, Di+1, Dk) which "leaked" from adjacent beamlets at times of about 280 ms, 500 ms, and 600 ms at different dose rates (DR1, DR2, DRk). Although the doses of each beamlet were deposited at an ultra-high dose rate greater than 1 Gy/s, the overall irradiation time (Dt) of said point is such that a mean dose deposition rate, DRa=S Dj/Dt can be lower than 1 Gy/s, thus losing the FLASH-RT effect. There is a danger in case the cumulated dose (S Dj) (of approximately 22 Gy according to the dotted line in FIG. 3(a)) is adequate when the FLASH-RT effect is present, but not at CDR. Since all individual doses were deposited at ultra-high dose deposition rate (HDR), the clinician may be of the impression that FLASH-RT effect was present thus sparing the healthy tissues. This impression, however, may be wrong in case the total dose was deposited over a period of time (Dt) such that at the mean deposition rate DRa<1 Gy/s, the cumulated dose was deposited at CDR instead of HDR, thus exceeding the dose admitted by the required NTCP at CDR.

The present disclosure solves the problem of ensuring that a target treated by PBS of charged particles is effectively irradiated at HDR where required taking account of any overlapping dose deposition distribution of all beamlets leaking over a given spot to be treated. These and other advantages will be described in more detail.

SUMMARY

The present disclosure concerns a treatment planning system (TPS) for generating a plan for treatment by radiation with charged particles beams, for instance with proton beams, applied by pencil beam scanning (PBS) onto a target tissue. The boundaries of the target tissue are defined within a peripheral surface which encloses tumoral cells, and which is surrounded by healthy cells and/or encloses also healthy cells. The healthy cells form healthy tissues. The treatment plan consists of N fractions of irradiation, with N≥1, and the treatment plan fulfils the following criteria. First, at the end of the N fractions, all tumoral cells of the target tissue (3t) must have received a total target dose (DmtT) equal to the sum of target fraction doses (Dmtj) received at each fraction (i.e., DmtT=Σ Dmtj), which is at least equal to a minimum target dose (DmtT0) for killing the tumoral cells, i.e., DmtT=Σ Dmtj DmtT0. Second, at the end of the N fractions, all healthy cells (3hi) of the healthy tissues surrounding or enclosed within the peripheral surface must have received a total healthy dose (DhTi) equal to the sum of the healthy fraction doses (Dhij) received at each fraction j (i.e., DhTi=Σ

Dhij), such that the healthy fraction dose (Dhij) received at each fraction j does not exceed a predefined fraction dose threshold for preserving the healthy cells at the end of the fraction j, and the total healthy doses (DhTi) received and cumulated at the end of the N fractions does not exceed a predefined total dose threshold for preserving the healthy cells at the end of the treatment of N fractions.

The TPS comprises a dose definition stage defining the doses to be deposited within the peripheral surface and in the direct surrounding thereof.

The TPS comprises a beam definition stage defining positions and dimensions of the beamlets of the PBS during the at least one high rate fraction, the beam definition stage comprising a definition of a diameter of a spot formed on a surface plane by a beamlet propagating along a beamlet axis substantially parallel to a beam direction and intersecting substantially perpendicularly the surface plane at a spot center, wherein the surface plane contacts the skin of the patient at least at the spot center, and a definition of a spot position pattern (x, y) on the surface plane of the spots formed by different beamlets substantially parallel to the beam direction such that the spots positions pattern (x, y) ensures that the spots cover a whole area defined within a projection parallel to the beam direction of the peripheral surface onto the surface plane.

The TPS also comprises a dose rate definition stage comprising at least one high rate fraction j, wherein specific volumes (Vs) bounded by a specific volume surface enclosing healthy cells and optionally tumoral cells are irradiated at a ultra-high dose deposition rate (HDR), defined as a dose deposition rate, HDR=Dj/t≥1 Gy/s, wherein Dj is a dose deposited during one fraction onto a specific volume and t is the time of deposition of the dose Dj.

The TPS differs from state of the art TPSs in that it also comprises a beamlets scanning sequence stage defining a scanning sequence of irradiation of the beamlets, the beamlets scanning sequence stage comprising an optimization of a time sequence of beamlets emission according to the spot positions pattern (x, y) defined in the beam definition stage such that at the end of a fraction j, a dose is deposited onto at least a predefined fraction, for instance at least 50%, or at least 75%, of each specific volume at a mean deposition rate (DRa) superior or equal to a predefined value (DRa0) of a mean ultra-high dose deposition rate boundary (DRa≥DRa0). A medical practitioner may define a threshold dose value below which a healthy cell is not at risk (or at least at limited risk). The treatment plan may favor those portions of each specific volume which receive a dose lower than or equal to the threshold dose value as the portions complementary to the predefined fraction into which a dose was not or could not be deposited at a value of DRa≥DRa0. This way, for example, a treatment plan may manage to deposit at DRa≥DRa0 doses higher than the threshold dose value over 60% of a specific volume, and at the same time, to deposit doses lower than the threshold dose value in 75% of the complementary 40% of the specific volume wherein doses were deposited at DRa<DRa0.

It follows that 60%+75%×40%=90% of the cells in the specific volume could be spared, either by depositing high doses at HDR (i.e., DRa≥DRa0), or by depositing low doses only, of limited impact on the cells' health. The value of the threshold dose value depends on the organ being irradiated, and on the patient in general (age, gender, weight, etc.) and can be defined by a clinician or medical practitioner.

The mean deposition rate DRa may be defined as, DRa=ΣDj/Δt≥DRa0≥1 Gy/s, wherein ΣDj is a sum of a percentile of all the doses deposited by one or more beamlets onto a given volume, wherein the percentile is at least 95%, or, in some embodiments, at least 98%, and Δt is the time between the first and last doses deposited onto the given volume.

In one embodiment, the beams definition stage comprises, a definition of a surface target outline and of surface healthy outlines formed by a projection onto the surface plane, parallel to the beam direction, of the peripheral surface of the target tissue, and peripheral surfaces of the healthy tissues surrounding the target tissue, and the spot diameter and spot positions pattern (x, y) on the surface plane may be determined to homogeneously cover an area enclosed within the surface target outline.

In this embodiment, the beam axes of two adjacent proton beamlets may be distributed according to the spot positions pattern (x, y) are separated from one another by a distance comprised between 1.2 and 2.5 times σ, or, in some embodiments 1.3 to 1.5 times σ, wherein $\sigma^2$ is the variance of a Gaussian dose distribution in the spots on the surface plane (P0) formed by the two adjacent proton beamlets.

In this embodiment, a first specific volume may extend along a distance Vz=(Zn−Z1) measured along the beam direction (z) from the surface plane. The beamlets scanning sequence stage may comprise a definition of n inner planes parallel to the surface plane and distributed at corresponding depths (Z1, . . . , Zn), between the depth Z1 at the level of the inner plane, and the depth (Zn) at a level of the $n^{th}$ inner plane such that the specific volume is sandwiched between the first and $n^{th}$ planes. It may also comprise a definition of a specific volume projection outlines formed by a projection onto the respective surface planes, parallel to the beam direction, of the corresponding specific volume surface, and a selection of the beam scanning sequence yielding for at least the predefined fraction of 50%, or in some embodiments at least 75% of a selected volume defined within a cylinder of base formed by the specific volume projection outline (V0) and of height Vz=(Zn−Z1), a mean dose deposition rate DRa≥DRa0. These may be repeated for each specific volume different from the first specific volume.

According to the present disclosure, the specific volumes may be defined according to one or more of the following: at least one specific volume contains cells located on either side of a portion of the peripheral surface most remote from the surface plane (P0) and crossed by the beams of the PBS to exit the target tissue, at least one specific volume referred to as an uncertain zone is defined as a zone comprising both tumoral and healthy cells intermixed at different ratios, at least one specific volume contains healthy cells of a healthy tissue (3hi) which are intersected by one or more beamlets of diameter.

In an embodiment of the disclosure, each specific volume may be comprised within a specific peripheral surface. The scanning sequence optimization for each specific volume may include steps to define a specific volume outline formed by a projection parallel to the beam direction of the specific peripheral surface of the specific volume onto the surface plane, define a sub-set of the spot position pattern (x, y) comprising the spots intersecting or included within the specific volume outline, deliver a dose to a first spot center crossed by a first beamlet, record the doses delivered by the first beamlet to neighboring spot centers, select a second spot center to be irradiated directly after the first spot center, such as to fulfil one or more of the following constraints, minimize $\Sigma_m$ (DRa(m)−DRT(m))$^2$, wherein DRT(m) is a target average dose rate for each spot (m), and/or maximize an average of the average dose rates (DRa(m)) over all the spots measured, and/or maximize the average dose rates (DRa(m)) of each spot (m), and repeat the foregoing steps with a third and following spots for all the spots of the sub-set of the spots position pattern (x, y).

In an alternative embodiment, each specific volume may be comprised within a specific peripheral surface and the sequence optimization for each specific volume may be determined by steps to define a specific volume outline formed by a projection parallel to the beam direction onto the surface plane, and define a sub-set of the spot position pattern (x, y) intersecting or included within the specific volume outline. The steps may also include to, for each position of the spot centers of the sub-set, assign an initial sequence ranking in the beam scanning sequence, define a value for a maximum ranking jump (h) a spot center can make in one permutation $\pi(p)$, i.e. $|p-q| \leq h$ define a first total permutation (u=1) of the initial sequence ranking of the spot centers composed of M local permutations $\pi(p)=q$ where p is an initial ranking of a given spot center in the initial sequence ranking and q a final ranking after the permutation, with a condition of maximum ranking jump (h), wherein the total permutation is composed of M such $\pi(p)$ permutations applied sequentially to the initial sequence. The steps may also include to define a weighted neighbor ranking distance of a spot center at a starting sequence ranking (p) as follows, define a weighted neighbor ranking distance (Dw(p, r)) between the spot center (cp) at the initial sequence ranking (p) and a spot center (cr) at a neighboring sequence ranking (r), as $Dw(p, r)=|p-r| \cdot Ir,p(r)$, where $|p-r|$ is a ranking difference (D(p, r)) between ranking sequences (p) and (r), and where Ir,p(r) is a dose (D) deposited onto the spot at position (cp) by a beam intersecting the position (cr). Further, the steps may include to define a total weighted neighbor distance (Dt(p)) from the spot center (cp) at the initial sequence ranking (p) to all spot centers at neighboring ranks thereof, as $Dt(p)=\Sigma_r Dw(p,r)$, calculate a cost (C,1(p, r)) of a local permutations $\pi(p)=q$ as, C,1(p, r)=Dt(q)−Dt(p), calculate a first total cost $Ct,1(\pi)=\Sigma_p C,1(p,r)$, of the first total permutation (u=1), define all possible second, third and successive total permutations (u=2, 3, 4, . . . ) of the initial sequence ranking for the chosen ranking jump (h), which are different from each other and from the first total permutation (u=1), for each of the second, third; and successive total permutations defined in the preceding step, calculate a corresponding second, third, and successive total costs, $Ct,u(\pi)=\Sigma_p C,u(p,r)$, and select the total permutation (u=1, 2, 3, . . . ) yielding the lowest total cost (Ct,u($\pi$)).

In yet an alternative embodiment, each specific volume may be comprised within a specific peripheral surface and the sequence optimization for each specific volume may be determined by steps to define a specific volume outline (V0) formed by a projection parallel to the beam direction of the specific peripheral surface of the specific volume onto the surface plane (P0), define a sub-set of the spot position pattern (x, y) comprising the spots intersecting or included within the specific volume outline, define a scarf sequence unit cell with the following steps, define an initial spot for being irradiated first by a first beamlet, define successive second, third, to $w^{th}$ spots, each sequentially adjacent to one another and all aligned along a width direction, define a $(w+1)^{th}$ spot as being adjacent to the $w^{th}$ spot along a length direction, different from, and in some embodiments normal to the width direction, define $(w+_2)^{nd}$ to $2w^{th}$ spots each sequentially adjacent to one another and all aligned along the width direction, define a $(2w+1)^{th}$ spot as being adjacent to the $2w^{th}$ spot along the length direction. The steps may be repeated N times for defining the scarf sequence unit cell, from an $(Aw+1)^{th}$ spot (S0v(Aw+1)) until a $((A+2)w+1)^{th}$ spot (S0v((A+2)w+1), with A=2 to (N+2), forming a first scarf of width (W) equal to a distance separating the first from the $w^{th}$ spots, and of length (L) equal to the distance separating the first from the $((N+4) w+1)^{th}$ spot, and wherein the width (W) of the scarf is limited by the constraint that the mean dose deposition rate (DRa) of the $2w^{th}$ spot is superior or equal to the predefined value (DRa0).

In another embodiment, the specific volume may have a width larger than the width of the first scarf, and that the scanning sequence optimization further includes defining a second and optionally a sequence of third and successive scarves, each parallel to the first scarf, and each adjacent to or slightly impinging with the preceding scarves in the sequence of first, second and successive scarves.

In an embodiment, the beam definition stage, the dose rate definition stage, and the beamlets scanning sequence stage may be determined by a pre-optimizer module separate from and interacting with a conventional TPS system determining the dose definition stage.

The dose rate definition stage may define a highest dose rate (DRmax) at which a given dose (Di) can be delivered by a beamlet, as, DRmax=8 Imax. K(E), wherein Imax is a maximum intensity (Imax) a nozzle of a proton accelerator can deliver, and K(E) is a known function relating the proton fluence to the incident energy of the proton beam.

According to the present disclosure, a single-beam treatment plan may be first determined using a single beam composed of several beamlets parallel to a first beam direction. In case less than the predefined fraction of the specific volume is irradiated with a mean dose deposition rate (DRa) superior or equal to the predefined value (DRa0), a multi-beam treatment plan is determined using two beams or more beams, each composed of several beamlets and each parallel to different beam directions, all secant to one another, until at least the predefined fraction of spots is irradiated at DRa>DRa0.

The dose definition stage may include the definition of an energy shaping device for defining beamlets having an optimized Sum of Bragg Peaks (SOBP) along the penetration depth (z) for each spot of the spot position pattern (x, y).

BRIEF DESCRIPTION OF THE FIGURES

FIG. 5(a) shows the same target tissue as in FIGS. 4(a) and 4(c) with a specific volume (Vs) to be irradiated at HDR.

FIG. 5(b) shows a sub-set of the spot position pattern (x, y) intersecting or included within the specific volume outline (V0).

FIG. 5(c) to 5(e) show the position of the target tissue and healthy tissue on a cut along the plane (x, z), the dose (Dj) and the mean dose deposition rate (DRa) deposited along the axis (z).

DETAILED DESCRIPTION

Figure 1A:
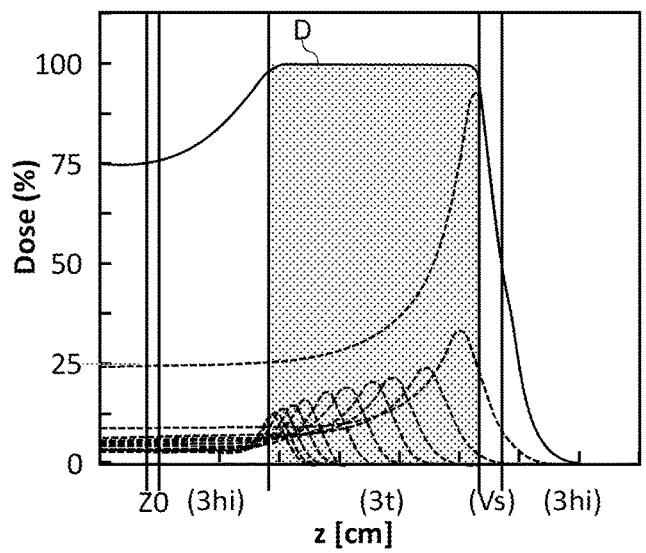
FIG. 1(a) shows the energy deposition onto tissues as a function of depth (z) of penetration for proton beamlets, adding up to form a sum of individual Bragg Peaks (SOBP) spanning over the whole depth of the tumour (3).
Figure 1B:
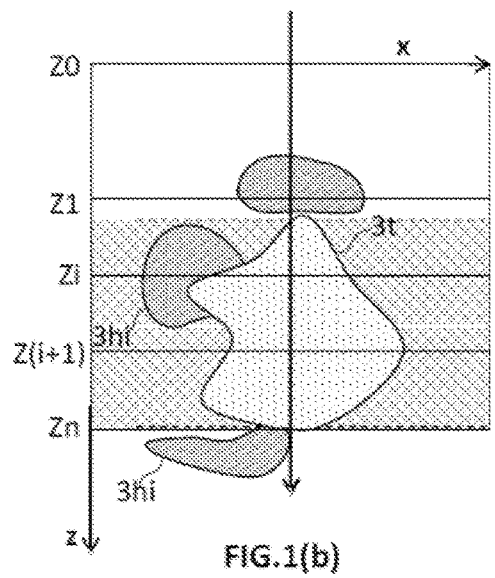
FIG. 1(c) shows the corresponding SOBP.
Figure 1C:
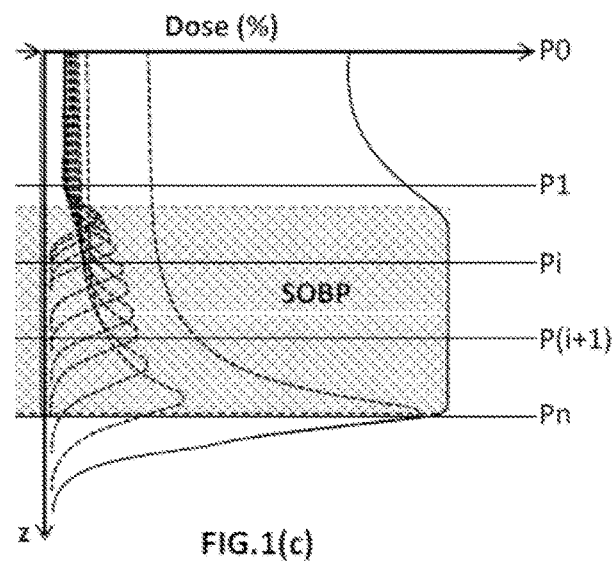

The present disclosure concerns a treatment planning system for generating a plan for treating with one or more charged particle beams of a target tissue (3t) delivered by pencil beam scanning (PBS). Examples of target tissues are illustrated in FIGS. 1(b), 4(a), 4(c), 5(a), 5(c), 6(a), and 6(b) comprising tumoral cells enclosed within a peripheral surface, which is surrounded by healthy cells and/or encloses also healthy cells, wherein the healthy cells form healthy tissues (3hi) wherein the subscript i designates the type of healthy tissues (3hi). Because of the complexity of the multi-parameter treatment to be planned, the TPS may comprise a computer or processor configured for generating the treatment plan, including for example, optimizing the nature and number of beams or beamlets required for fulfilling predefined criteria. The nature of the beam includes the type of charged particles, the intensity of the beam, the doses to be deposited, the dose deposition rates, the direction of the beams, the number and frequency of fractions, and the like. Because of the dose deposition profile including a Bragg peak as illustrated in FIGS. 1(a) and 1(c), the charged particles may be protons. The charged particle beam or beams according to the present disclosure are delivered by pencil beam scanning (PBS). The plan consists of N fractions of irradiation, with $N \geq 1$, the TPS must optimize the nature and number of beam irradiations fulfilling the following criteria.

Figure 2A:
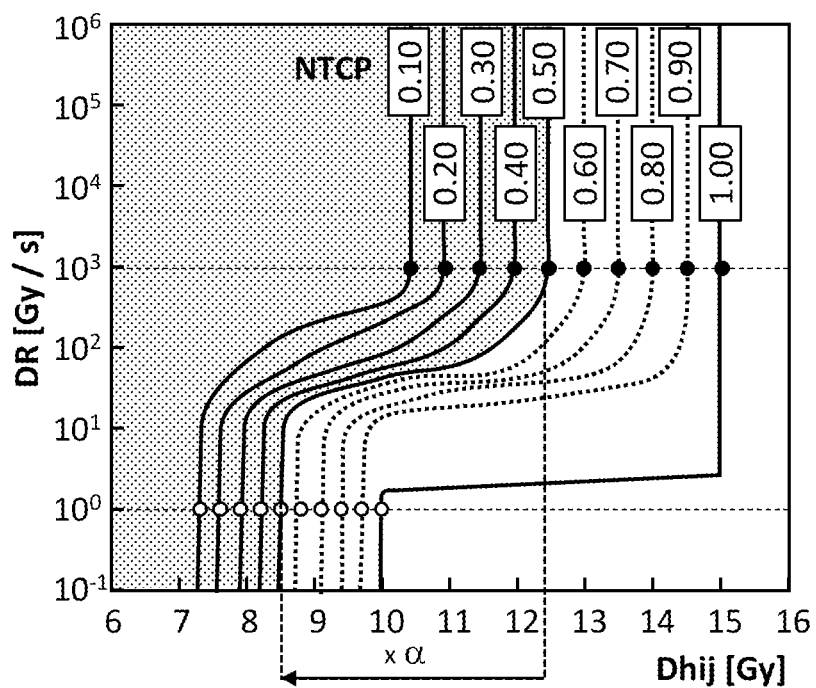
FIG. 2(a) shows iso-NTCP-lines as a function of dose (D) deposited into a healthy tissue and of the dose deposition rate (DR).
Figure 2B:
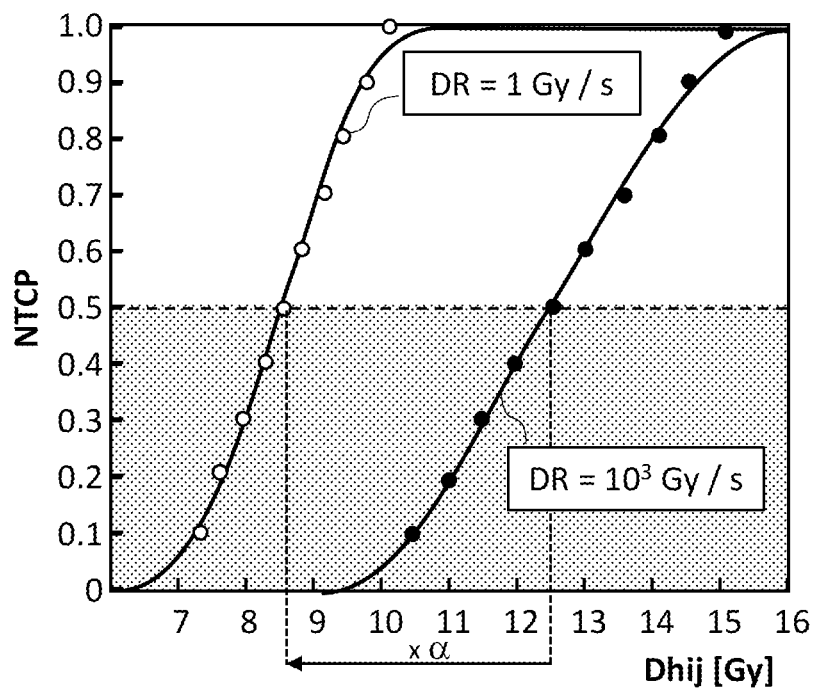
FIG. 2(b) plots NTCP as a function of dose (D) deposited into a healthy tissue at CDR (white circles) and at HDR (black circles).

First at the end of the N fractions, all tumoral cells of the target tissue (3t) must have received a total target dose (DmtT) equal to the sum of target fraction doses (Dmtj) received at each fraction (i.e., DmtT=$\Sigma$ Dmtj), which is at least equal to a minimum target dose (DmtT0) for killing the tumoral cells, i.e., DmtT=$\Sigma$ Dmtj DmtT0. Second, at the end of the N fractions, all healthy cells (3hi) of the healthy tissues surrounding or enclosed within the peripheral surface must have received a total healthy dose (DhTi) equal to the sum of the healthy fraction doses (Dhij) received at each fraction j (i.e., DhTi=$\Sigma$ Dhij), such that, the healthy fraction dose (Dhij) received at each fraction j does not exceed a predefined threshold for preserving the healthy cells at the end of the fraction j, and the total healthy doses (DhTi) received and cumulated at the end of the N fractions does not exceed a predefined threshold for preserving the healthy cells at the end of the treatment of N fractions While the FLASH effect is now commonly acknowledged by the persons skilled in the art, the chemical mechanisms underlying the FLASH effect are still elusive. Several different theories have been advanced. For example, it has been proposed that the ultra-high dose deposition rate FLASH-RT significantly reduces the killing of cells circulating in the bloodstream, suggesting that the threshold dose deposition rate separating CDR and HDR could depend on the blood circulation time for one cycle. For humans, a threshold dose deposition rate of about 1 Gy/s has been reported for the FLASH effect to appear. It has also been proposed that organic peroxyl radicals ROO. formed by addition of $O_2$ to primary carbon-centered radicals could play a major role in radio-induced complications. In another example, it has also been reported that the competition between the radio-induced oxygen depletion and the oxygen rediffusion from capillaries could explain the FLASH effect. The present disclosure is not bound by any one of these or other theories and is based on the experimental evidence that the FLASH effect actually exists. The present disclosure was developed based on the following observations. First, tumoral cells are killed similarly, independently of the dose deposition rate (DR). Second, a predefined Normal Tissue Complication Probability (NTCP0i) of a healthy tissue (3hi) not to be exceeded is reached at lower doses deposited at conventional dose deposition rates (CDR) than it is at ultra-high dose deposition rates (HDR), as shown in FIGS. 2(a) to 2(b). Third, tumoral cells in target tissues (3t) have a longer recovery time than healthy tissues exposed to a same radiation dose, regardless of the dose deposition rate.

In order to fulfil the foregoing criteria, the TPS may comprise a dose rate definition stage comprising at least one high rate fraction j, wherein one or more specific volumes (Vs) including healthy cells and optionally tumoral cells are irradiated at a ultra-high dose deposition rate (HDR), defined as a dose deposition rate, HDR=Dj/t$\geq$1 Gy/s, wherein Dj is a dose deposited during one fraction onto a specific volume and t is the time of deposition of the dose Dj.

The TPS may also comprise a beam definition stage defining positions and dimensions of the beamlets of the PBS during the at least one high rate fraction, the beam definition stage comprising a definition of a diameter (D) of a spot (PBk) formed on a surface plane (P0) by a beamlet propagating along a beamlet axis substantially parallel to a beam direction and intersecting substantially perpendicularly the surface plane (P0) at a spot center (cp, cr), wherein the surface plane (P0) contacts the skin of the patient at least at the spot center, and a definition of a spot position pattern (x, y) on the surface plane (P0) of the spots (PBk) formed by different beamlets substantially parallel to the beam direction such that the spots positions pattern (x, y) ensures that the spots cover a whole area defined within a projection parallel to the beam direction of the peripheral surface onto the surface plane (P0).

The TPS may also comprise a dose definition stage defining the doses deposited along the beam direction by each beamlet required for fulfilling the criterion (C1).

Figure 3A:
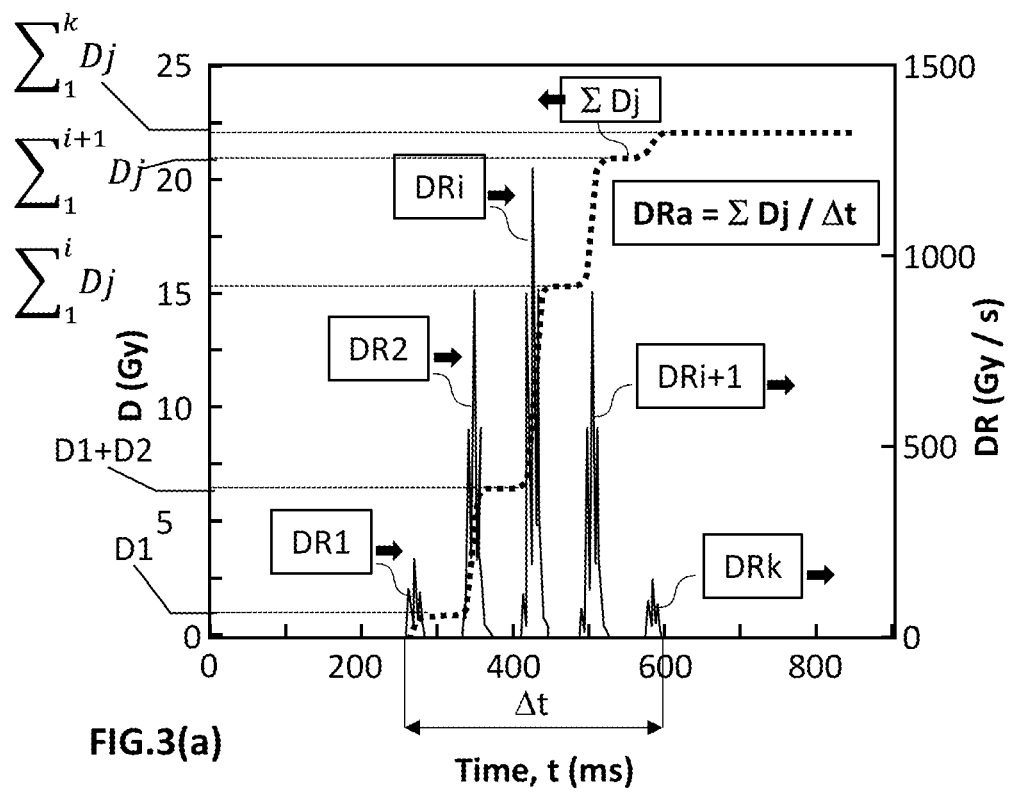
FIG. 3(a) shows the effect on overlapping dose distribution spots on the mean dose deposition rate (DRa).

When irradiating a specific volume (Vs) with beamlets by PBS, although each beamlet can deposit doses at ultra-high dose deposition rate (HDR), because of the overlapping of the spots defining the dose distribution on planes normal to the beam direction (z), which increases the radiation time (Δt) of a given volume as shown in FIG. 3(a), to a point wherein the mean dose deposition rate (DRa) becomes lower than a predefined mean ultra-high dose deposition rate boundary (DRa≥DRa0), required by the plan to ensure that the treatment plan fulfils a predefined NTCP value.

To solve the foregoing problem, the TPS of the present disclosure further comprises a beamlets sequence stage defining a sequence of irradiation of the beamlets. The beamlets sequence stage comprises a sequence optimization of a time sequence of beamlets emission according to the spot positions pattern (x, y) defined in the beam definition stage such as to yield for at least a predefined fraction of the spots included in or intersecting each specific volume a mean dose deposition rate (DRa) which is superior or equal to a predefined value (DRa0) defining a mean ultra-high dose deposition rate boundary (DRa≥DRa0≥1 Gy/s). The predefined fraction may be is 50%, or in some embodiments, 75% or, 90%, 95%, or 98%, and DRa is defined as, DRa=ΣDj/Δt≥DRa0≥1 Gy/s, wherein ΣDj is a sum of a percentile of all the doses deposited by one or more beamlets onto a volume or spot, and Δt is the time between the first and last doses deposited onto said volume or spot. The percentile may be at least 95%, at least 98%, or 100% depending on the specific cases, of the total sum of doses Dj. The exact value of the percentile between 95 and 100% can easily be defined by a skilled person depending on the situation (e.g., distribution and values of the doses deposited as a function of time as shown in FIG. 3(a)).

The various stages of the TPS of the present disclosure are described more in detail in continuation.

Dose Definition Stage

The dose definition stage may be performed by an oncologist who identifies the geometry of the peripheral surface enclosing the tumoral cells based on images of the tumour region obtained by computed tomography scan (=CT-scan). The dose definition stage defines the doses to be deposited within the peripheral surface and in the direct surrounding thereof, required for killing the tumoral cells comprised within the peripheral surface. This stage may be well known to the person skilled in the art. This operation is also referred to as a definition of the spot weights.

In an embodiment, the dose definition stage assumes the use of an energy shaping device for defining beamlets having an optimized Sum of Bragg Peaks (SOBP) along the penetration depth (z) for each spot of the spot position pattern (x, y). The actual geometry of the energy shaping device may be computed after the dose definition stage. As the diameter of the different sections of cylinders composing an energy shaping device are related to the weight of the spots, the weight of the spots may be optimized before the shape of the energy shaping device can be computed in order to obtain the desired spot weights Dose Rate Definition Stage The dose rate definition stage defines the dose rates at which doses are to be deposited locally to simultaneously kill the tumoral cells and spare as much as possible the healthy cells profiting of the FLASH effect. This definition is generally performed by an oncologist who identifies one or more specific volumes (Vs) comprising healthy cells based on images of the tumour region obtained by computed tomography scan (=CT-scan). To reach a FLASH effect in the one or more specific volumes (Vs), the TPS delivers at least one high rate fraction j, wherein the one or more specific volumes (Vs) are irradiated at a ultra-high dose deposition rate (HDR), HDR is defined as a dose deposition rate, HDR=Dj/t≥1 Gy/s, wherein Dj is a dose deposited during one fraction onto a specific volume and t is the time of deposition of the dose Dj.

In an embodiment, the dose rate definition stage may take into account the performance of the particle treatment system available for carrying out the plan. For example, the dose rate definition stage can define a highest dose rate (DRmax) at which a given dose (Di) may be delivered by a beamlet, as, DRmax=8 Imax,·K(E), wherein Imax is a maximum intensity a nozzle of a proton accelerator can deliver, and K(E) is a known function relating the proton fluence (number of protons per cm$^2$) to the dose deposited by the proton beam in the tissues for different incident energies (E) of the proton beam. For example, in Equation 26 in "Bortfeld, T. (1997) An analytical approximation of the Bragg curve for therapeutic proton beams. Med. Phys., 24(12), 2024-2033" the factor on the right of $\phi_0$ represents K(E). The dose rate definition stage can also define the maximum scanning speed, i.e. the maximum speed at which the spot can move from one location to another in a plane normal to the proton beam.

With a chart of the localisation of the doses and dose rates required to treat the tumour, the next stage may be to define the characteristics of one or more beams required for implementing the chart. This stage is defined in the beam definition stage.

Beam Definition Stage

The beam definition stage defines the type of charged particles to be irradiated (e.g., protons), the number N of fractions j comprised by the treatment, and the positions and dimensions of the beamlets of one or more beams of the PBS during the at least one high rate fraction, This stage also defines the number of beams and beam directions (z, z1, z2), the superposition of coaxial beamlets to define the shape of the SOBP as a function of the geometry of the target tissue (3t) produced by each beamlet, the intensity of the beamlets, and the like. The beam definition stage comprises at least two steps, including a definition of a diameter (d) of a spot (S01, S02) formed by one or a series of coaxial beamlets, and a definition of a spot position pattern (x, y) on the surface plane (P0)

Diameter (d) of a Spot

Figure 3B:
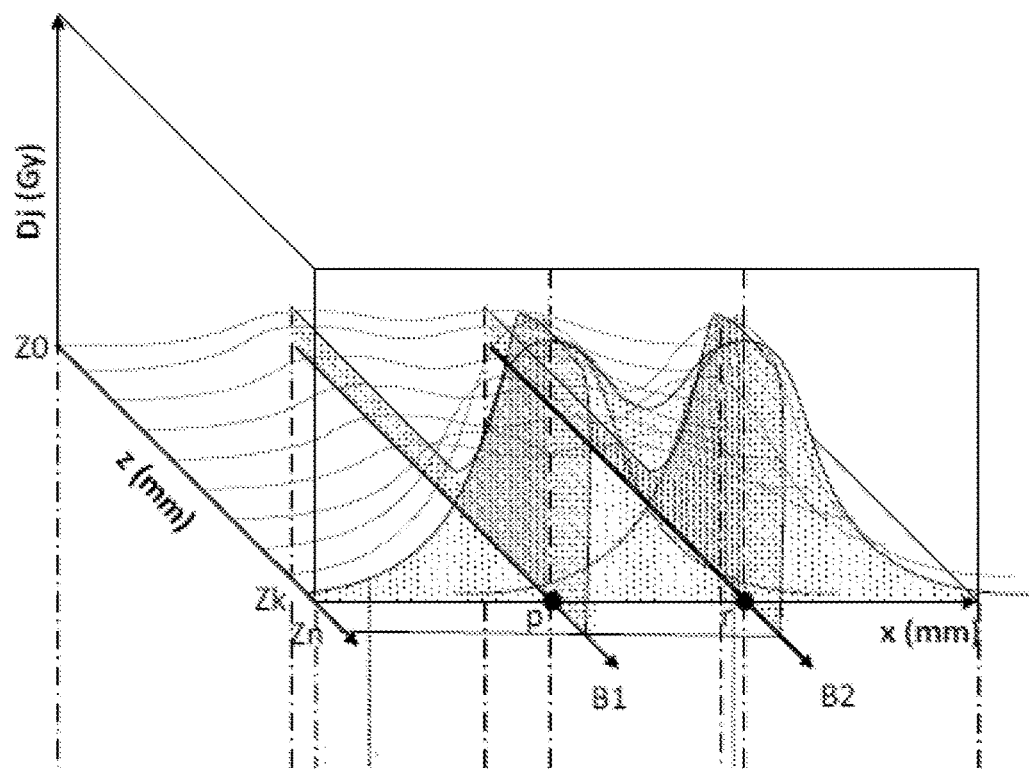
FIG. 3(b) shows the doses deposited over a plane (x, z) by two proton beamlets (B1, B2), with overlapping gaussian dose distribution curves along the axis (x).

A spot (S01, S02) of diameter (d) is formed on a surface plane (P0) by a beamlet (B1, B2) propagating along a beamlet axis substantially parallel to a beam direction and intersecting substantially perpendicularly the surface plane (P0) at a spot center (cp, cr), wherein the surface plane (P0) contacts the skin of the patient at least at the spot center. The diameter of a spot depends on the dose distribution deposited on the surface plane (P0) by said beamlet. The dose distribution on the surface plane follows a substantially normal or Gaussian distribution, as illustrated in FIG. 3(b), centered on the intersection point (cp, cr) of the beamlet axis with the surface plane (P0) and of variance $\sigma^2$. The dose (Dj) deposited by a beamlet at any given depth (Zk, with k=0−n) is maximal at an intersection point (cp, cr), between the beamlet axis and the corresponding plane (Pk, with k=0−n). The spot diameter (d) may be defined as d=2×(2 σ) centered on the corresponding spot center (cp, cr), which comprises 95.4% of the dose distribution or, alternatively, d=2×(3σ), which comprises 99.7% of the dose distribution. The spot diameter may be defined as $d=2\times(2\sigma)$.

Figure 3C:
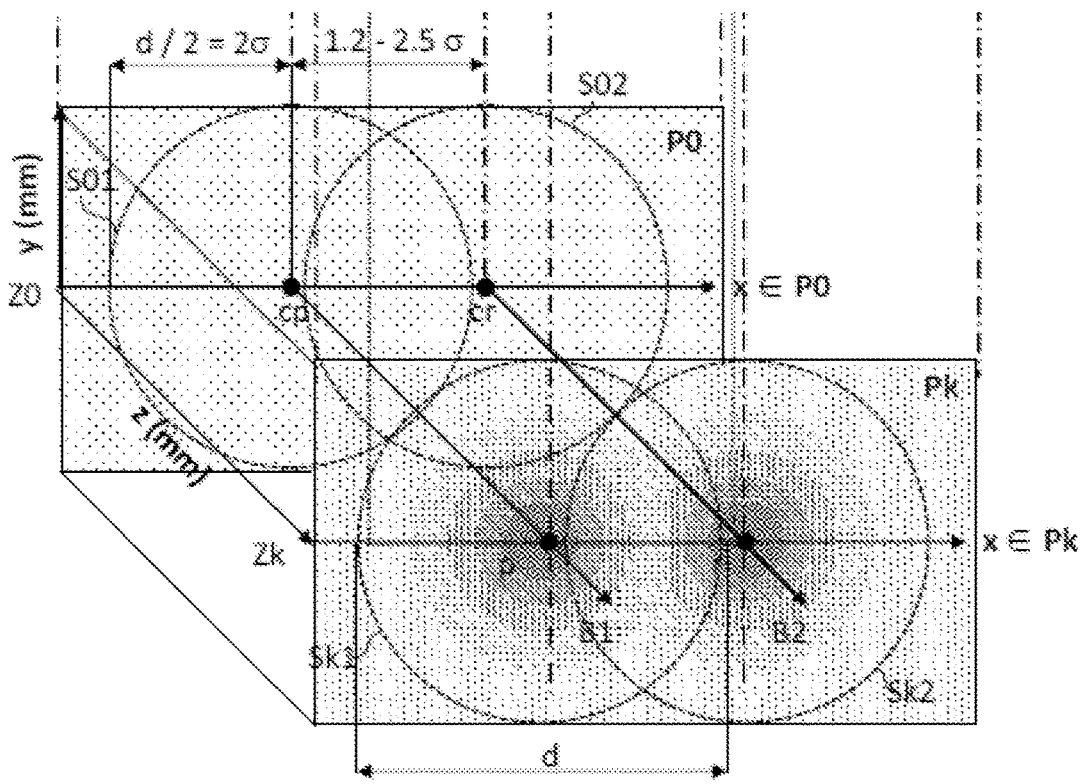
FIG. 3(c) shows a 3D view (x, y, z) of the approximately cylindrical propagation of the two beams (B1, B2) along the beam direction (z), the shades of grey illustrating the doses deposited on a plane (Pk) located at a depth (Zk) from the surface of the skin of a patient.

As illustrated in FIG. 3(b), a beamlet (B1, B2) deposits only a limited dose at the surface plane (P0) and deposits substantially the whole dose within a limited depth portion defined by the shape of the corresponding SOBP. It is first assumed that the shape of the dose distribution can be considered as remaining a gaussian all along the penetration depth (z) varying only on the value of the maximum dose deposited centered on the beamlet axis. The maximum dose as a function of the penetration depth (z) is defined by the corresponding SOBP. It is further assumed that, as shown in FIG. 3(c), the diameter of each spot is approximately independent of the penetration depth (z) or, in other words, that each beamlet propagates along a cylinder. This is not strictly correct, as it was observed that beamlets tend to flare out a bit as they penetrate deeper into a patient's body. The cone thus formed has a very low aperture and can therefore be safely approximated as forming a cylinder for the purpose of optimizing the spot sequence. This approximation, however, may not be agreeable for other computations, such as accurately computing the dose distribution as a function of depth. In such cases, a more accurate definition of the spot diameter as a function of depth is required, which is quite straightforward to establish.

Note that the spot diameter (d) is herein measured at the surface plane (P0) because this is a fixed plane independent of the location and geometry of the peripheral surface. It is clear that the same exercise can be performed on any plane along the penetration depth (z) of the beamlet. Since the two assumptions supra are correct at least as a first approximation, very similar results would be obtained independently of the penetration depth (z) the plane taken as reference intersects the central axis of the beamlet (B1, B2).

Spot Position Pattern (x, y)

Figures 4A, 4B:
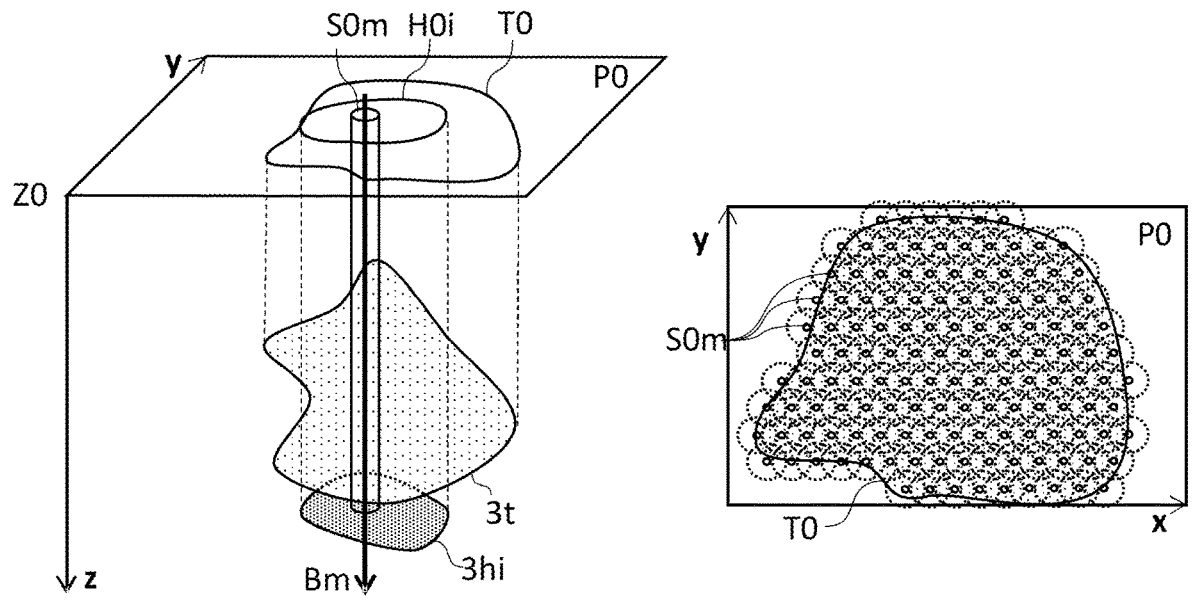
FIG. 4(a) illustrates a target tissue (3t) comprising tumoral cells enclosed within a peripheral surface, which is surrounded by healthy cells (3hi) and/or encloses also healthy cells (3hi), which is irradiated by a beamlet (Bm) forming a spot (S0m) on a plane (P0) intersecting the beamlet (Bm) at the level of a skin of a patient.
FIG. 4(b) shows a spot position pattern (x, y) on the surface plane (P0).
Figure 7:
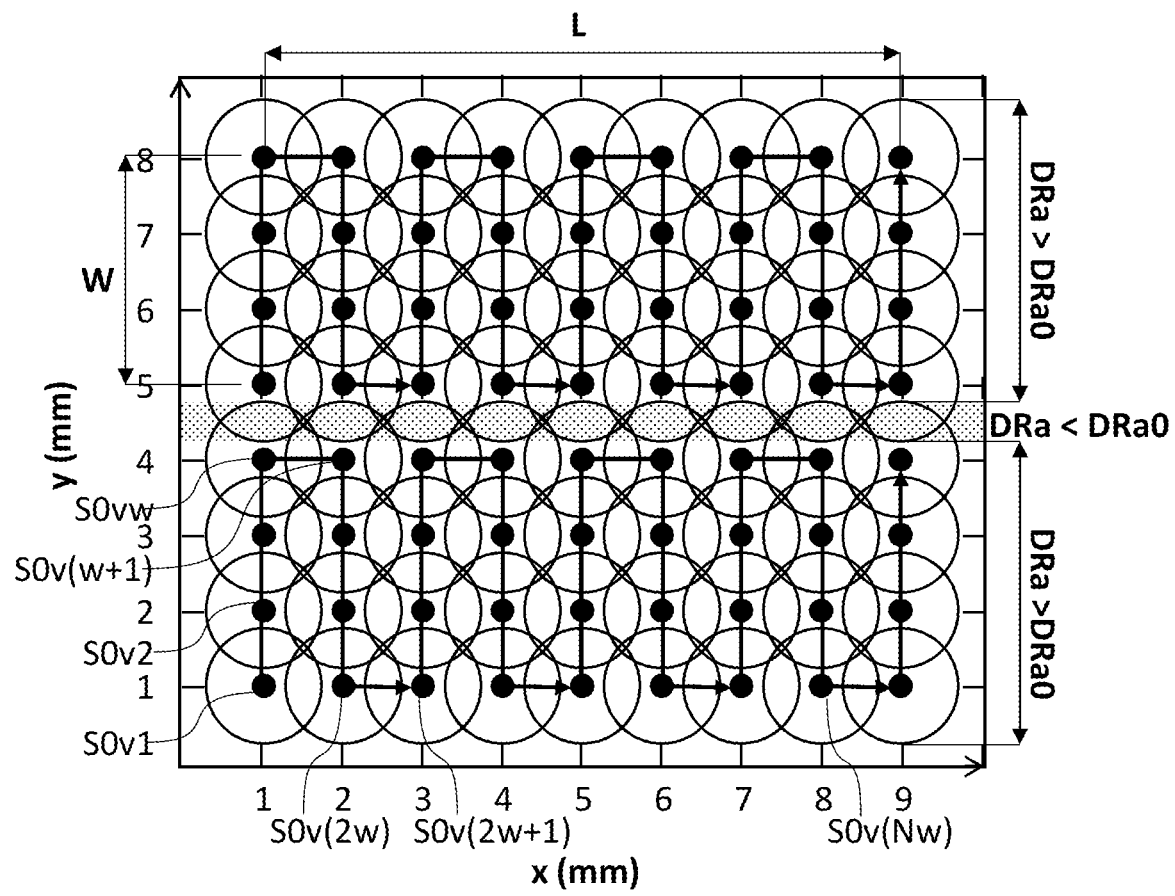
FIG. 7 shows a beamlets sequence defining two slightly overlapping scarves.

Irradiation by pencil beam scanning (PBS) may require a spot position pattern (x, y) to be defined on the surface plane (P0) of the spots (S01, S02) formed by different beamlets substantially parallel to the beam direction. The spots positions pattern (x, y) must ensure that the spots and corresponding beamlets cover an entirety of the target tissue (3t). This can be achieved by defining a surface target outline (T0) and a surface healthy outlines (H0i) formed by a projection onto the surface plane (P0), parallel to the beam direction, of the peripheral surface of the target tissue (3t), and peripheral surfaces of the healthy tissues (3hi) surrounding the target tissue (3t). Knowing the spot diameter (d), the spot positions pattern (x, y) on the surface plane (P0) is determined to homogeneously cover an area enclosed within the surface target outline (T0). An example of spot position pattern (x, y) is schematically illustrated in FIGS. 4(b) and 7.

A homogeneous covering of the area enclosed within the surface target outline (T0) can be obtained by separating from one another the beamlet axes of two adjacent proton beamlets distributed according to the spot positions pattern (x, y) by a distance comprised between 1.2 and 2.5 times 6, or 1.3 to 1.5 times $\sigma$, wherein $\sigma^2$ is the variance of the Gaussian dose distribution in the spots on the surface plane (P0) formed by the two adjacent proton beamlets. The distances separating two adjacent spot axes needs not be constant for all pair of adjacent spots, and they can vary from one another to fit the geometry of the peripheral surface. Regular arrays of spots of equal diameter only are illustrated in the Figures for sake of simplicity. It is clear that the beam definition stage can define spots of different diameters and distributed according to any pattern or even randomly, as long as the whole volume of the target tissue (3t) is thus covered.

As shown in FIG. 3(b) such spot positions pattern on a line parallel to the axis (x) yields a wavy dose distribution pattern with maxima at the level of the beamlets axes, and with minima at mid-distance between two adjacent beamlet axes. The dose distribution pattern becomes more complex when the PBS scans a second series of spots parallel to the axis (x) and offset with respect to the beamlets (B1, B2) represented in FIG. 3(b), depending on whether the beamlets in the second line are aligned or staggered with respect to the beamlets of the first line. This depends on the spot positions pattern (x, y) defined by the TPS.

With the foregoing stages, (viz., dose definition stage, dose rate definition stage, and beam definition stage) the first criterion (C1) can be fulfilled, that at the end of the N fractions, all tumoral cells of the target tissue (3t) must have received a total target dose (DmtT) which is sufficient to kill all tumoral cells (i.e., $DmtT=\Sigma\,Dmtj \geq DmtT0$). These stages alone, however, do not guarantee the sparing by the FLASH effect of healthy cells enclosed within the one or more specific volumes identified in the dose rate definition stage, because the mean dose rate (DRa) may become lower than required if the time separating the first dose from the last dose deposited onto a given point is longer than required to yield $DRa \geq DRa0 \geq 1$ Gy/s. The TPS of the present disclosure may include an additional stage designed for ensuring that $DRa \geq DRa0$ for at least a predefined fraction of each of the one or more specific volumes (Vs). This additional stage is referred to as beamlets scanning sequence stage.

Beamlets Scanning Sequence Stage

The TPS of a beamlets-scanning sequence stage may ensure that the scanning sequence guarantees that a dose is deposited onto at least a predefined fraction of at least 50%, or at least 75%, of each specific volume (Vs) at a mean dose deposition rate (DRa) superior or equal to a predefined value (DRa0) of the mean ultra-high dose deposition rate boundary ($DRa \geq DRa0 \geq 1$ Gy/s). The mean dose deposition rate DRa may defined as, $DRa = \Sigma Dj/\Delta t \geq DRa0 \geq 1$ Gy/s, wherein $\Sigma Dj$ is a sum of a percentile of all the doses deposited by one or more beamlets onto a given volume or spot and $\Delta t$ is the time between the first and last percentile of doses deposited onto the given volume or spot, as illustrated in FIG. 3(a). The percentile may be at least 95%, or at least 98% of the doses cumulative dose deposited.

Defining a percentile of the dose delivered during the fraction allows small doses deposited at one spot to be ignored, which cause limited damage to the healthy cells, but substantially increase the total irradiation time ($\Delta t$), artificially bringing DRa below DRa0, in cases where the FLASH effect would be present. For example, referring to FIG. 3(a), considering all doses represented as peaks DR1 to DRk (i.e., percentile=100%) deposited onto a spot over a total time $\Delta t$ yields a first value (DRa100) of the mean dose deposition rate into the spot. Now, the doses corresponding to the peaks DR1 and DRk are visibly very low compared with the doses corresponding to the peaks DR2, DRi, and DRi+1 (cf. dotted cumulative dose curve of FIG. 3(a)). Considering a percentile<100%, e.g., 95% or 98% would exclude the small doses corresponding to peaks DR1 and DRk, thus reducing slightly the value of the numerator ($\Sigma Dj$). On the other hand, the total time ($\Delta t$) at the denominator would thus be reduced substantially. The resulting value of $DRa95 = \Sigma Dj/\Delta t$ for a percentile of 95% may therefore be substantially higher than DRa100 (i.e., DRa95>>DRa100). Since the doses excluded from a percentile of 95% would account for only 5% of the total dose, it can safely be assumed that they have a limited damaging effect on the healthy cells compared with the other doses. Consequently, the FLASH effect is actually present with the deposition of the doses corresponding to the peaks (DR2, DRi, DRi+1), deposited within a shorter period (Δt).

The specific volumes (Vs) may be defined by a clinician. It may include healthy cells, which are to be irradiated at HDR to decrease the corresponding NTCP. In one embodiment, the specific volume includes the whole target tissue (3t) defined within the peripheral surface and a safety layer surrounding part or all of the peripheral surface and containing healthy cells. Note that the peripheral surface may also enclose healthy cells too. This embodiment can be implemented for target tissues of small dimensions, because irradiating at HDR becomes difficult for a given particle therapy systems when the dimensions of the specific volume increase. If the dimensions of the target tissue (3t) reach or exceed the capacity of the particle therapy system used to implement the TPS, it is possible to include one or more specific volumes (Vs) of reduced dimensions, so that each specific volume can be irradiated at HDR by the particle therapy system.

For example, the specific volumes (Vs) may be defined according to one or more of the following criteria. A first type of specific volume (Vs) may be a volume containing cells located on either side of a portion of the peripheral surface most remote from the surface plane (P0) and crossed by the beams of the PBS to exit the target tissue (3t). This is the embodiment illustrated in FIGS. 4(a) and 4(c), 5(a) to 5(e), and 6(a) to 6(g). This specific volume is particularly important in case the healthy tissue (3hi) is sensitive to radiations, and is in contact or directly adjacent to the peripheral surface, since the tumoral cells within the peripheral surface must be killed, and the healthy tissue (3hi) must be spared, with sometimes a few millimetres separating the tumoral cells from the healthy cells.

A second type of specific volume (Vs) is called an uncertain zone (3z) and is defined as a zone comprising both tumoral and healthy cells intermixed at different ratios. Since it contains tumoral cells, the uncertain zone (3z) is at least partly located within the peripheral surface. The healthy and tumoral cells are intermixed, or the uncertain zone can also form small islands or clusters of healthy cells within the peripheral surface. This kind of volume is also very critical, since there is no clear boundary separating tumoral cells from healthy cells. To date, the healthy cells contained in an uncertain zone (3z) may be sacrificed to ensure the killing of the tumoral cells mixed therewith.

A third type of specific volume (Vs) is a volume containing healthy cells of a healthy tissue (3hi) which are intersected by one or more beamlets of diameter (d). These healthy cells can be more remote from the peripheral surface, but due to several beams or beamlets crossing such volume, the healthy cells may be dangerously exposed to radiations.

In an embodiment illustrated in FIGS. 6(a) to 6(g), a first specific volume (Vs) extends along a distance Vz=(Zn−Z1) measured along the beam direction (z) from the surface plane (P0). In this embodiment, the beamlets scanning sequence stage comprises steps to provide a definition of n inner planes (P1, . . . , Pn) parallel to the surface plane (P0) and distributed at corresponding depths (Z1, . . . , Zn), between the depth Z1 at the level of the inner plane (P1), and the depth (Zn) at a level of the $n^{th}$ inner plane (Pn), such that the specific volume (Vs) is sandwiched between the first and $n^{th}$ planes (P1, Pn), a definition of a specific volume projection outlines (V0) formed by a projection parallel to the beam direction onto the surface plane (P0) or on the respective inner planes (P1, . . . Pn), of the corresponding specific volume surface, and a selection of the beam scanning sequence yielding a mean dose deposition rate DRa≥DRa0 for at least the predefined fraction of at least 50%, or at least 75% of a selected volume defined within the cylinder of base formed by the specific volume projection outline (V0) and of height Vz=(Zn−Z1).

The foregoing steps are repeated for each specific volume (Vs) different from the first specific volume. It is clear that, throughout the present document, the discussion based on the first specific volume applies mutatis mutandis to all specific volumes (Vs) identified and defined in the TPS.

As can be seen in FIGS. 6(c) to 6(g), the intersecting volume outlines (V2−V(n−1)) formed by an intersection of the first specific volume with the second to $(n-1)^{th}$ planes are all enclosed within the volume projection outline (V0) of the first specific volume (and all specific volumes). With its cylindrical geometry, the selected volume is therefore larger than the corresponding first specific volume (Vs) which is inscribed therein.

Figure 6A:
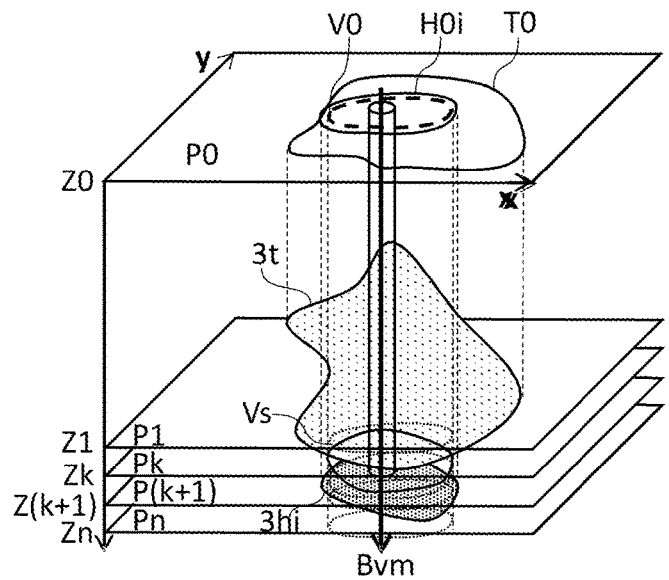
FIG. 6(a) shows the same target tissue as in FIGS. 4(a) and 5(a), with inner planes P1-Pn, intersecting a specific volume (Vs).
Figure 6B:
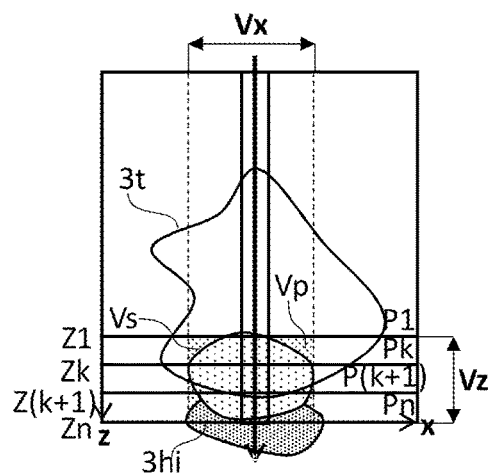
FIG. 6(b) shows a cut along the plane (x, z) of the target tissue of FIG. 6(a).
Figure 6C:
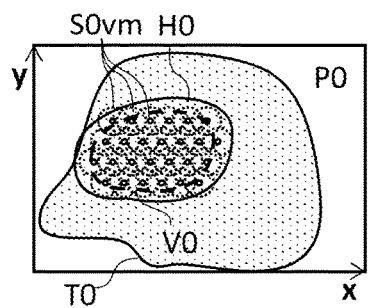
FIG. 6(c)-6(g) shows on the planes (P0-Pn) the projections of the target outline (T0) and specific volume outline (V0), as well as the intersection (T1-Tn) of the target tissue (3t) and the intersections (V1-Vn) of the specific volume (Vs) with the corresponding planes (P1-Pn).
Figure 6D:
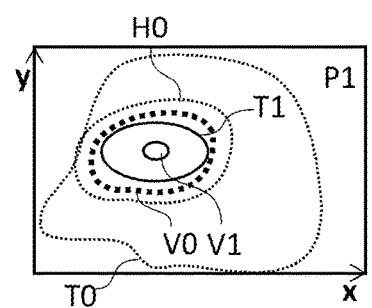
Figure 6E:
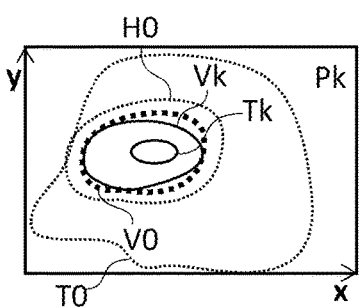
Figure 6F:
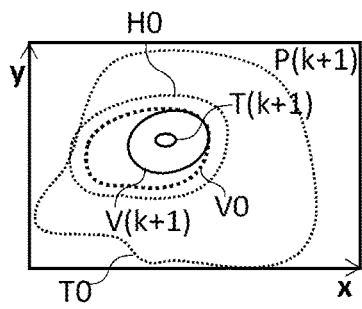
Figure 6G:
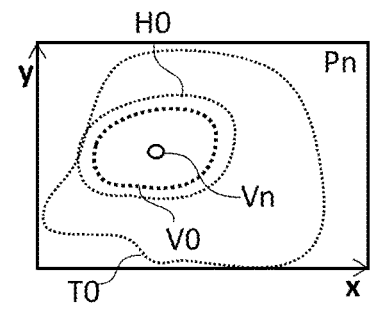

Selection of the beam scanning sequence yielding DRa≥DRa0 for at least the predefined fraction of each selected volume (Vs) can be achieved by different methods. Initial steps prior to implementing any of the following methods may include steps to provide the definition of a specific volume projection outline (V0) formed, as described supra, by a projection parallel to the beam direction onto the surface plane (P0) and the definition of a sub-set of the spot position pattern (x, y) comprising the spots (S0vk) intersecting or included within the specific volume outline (V0), as illustrated in FIGS. 5(b) and 6(c).

Selection of the Beam Scanning Sequence—Local Optimization Method

A first method for selecting a beam scanning sequence yielding DRa≥DRa0 for at least the predefined fraction of each selected volume (Vs) is the local optimization method. As a computation of DRa for all possible sequences would require extensive computational power, the present method optimizes each step sequentially, aiming at maintaining as high a value of DRa as possible at each sequential step. As mentioned in the preceding section, each specific volume (Vs) is comprised within a specific peripheral surface and the sequence optimization for each specific volume (Vs) may be initiated with the steps to, define a specific volume outline (V0) formed by a projection parallel to the beam direction onto the surface plane (P0), define a sub-set of the spot position pattern (x, y) intersecting or included within the specific volume outline (V0).

A dose is delivered to a first spot center (cp) of the sub-set which is crossed by a first beamlet (B1) and the doses delivered by the first beamlet to neighboring spot centers (cr) are recorded. The first spot may be located adjacent to the specific volume outline (V0), or in some embodiments at a corner of the outline (V0). If the first spot is not adjacent to or at a corner of the outline (V0), the algorithm may choose a sequence that leads the following spots towards the outline or towards a corner thereof, if any.

A second spot center (cr) of the sub-set is selected to be irradiated directly after the first spot center (cp), such as to fulfil one or more constraints including minimize $\Sigma_m (DRa(m)-DRT(m))^2$, wherein DRT(m) is a target average dose rate for each spot (m), and/or maximize an average of the average dose rates (DRa(m)) over all the spots measured, and/or maximize the average dose rates (DRa(m)) of each spot (m), and repeat the foregoing steps with a third and following spots for all the spots of the sub-set of the spots position pattern (x, y).

The local optimization method may be straightforward and easy to implement, requiring moderate to low computational power.

Selection of the Beam Scanning Sequence—Permutation Method

An alternative method for selecting a beam scanning sequence yielding DRa≥DRa0 for at least the predefined fraction of each selected volume (Vs) is the permutation method. As mentioned supra, each specific volume (Vs) is comprised within a specific peripheral surface and the sequence optimization for each specific volume (Vs) may be initiated with steps to define a specific volume outline (V0) by a projection parallel to the beam direction onto the surface plane (P0), define a sub-set of the spot position pattern (x, y) intersecting or included within the specific volume outline (V0).

For each position of the spot centers (cp, cr) of the sub-set, an initial sequence ranking is assigned in the beam scanning sequence. A value is defined for a maximum ranking jump (h) a spot center can make in one permutation $\pi(p)$, i.e. $|p-q| \leq h$.

A first total permutation (u=1) of the initial sequence ranking of the spot centers is defined, which may be composed of M local permutations $\pi(p)=q$ where p is an initial ranking of a given spot center in the initial sequence ranking and q a final ranking after the permutation, with a condition of maximum ranking jump (h). The total permutation is composed of M such $\pi(p)$ permutations applied sequentially to the initial sequence.

A weighted neighbor ranking distance of a spot center (cp, cr) at a starting sequence ranking (p) may be defined by steps to define a weighted neighbor ranking distance (Dw(p, r)) between the spot center (cp) at the initial sequence ranking (p) and a spot center (cr) at a neighboring sequence ranking (r), as $Dw(p, r)=|p-r| \cdot Ir,p(r)$, where $|p-r|$ is a ranking difference (D(p, r)) between ranking sequences (p) and (r), and where Ir,p(r) is a dose (D) deposited onto the spot at position (cp) by a beam intersecting the position (cr), define a total weighted neighbor distance (Dt(p)) from the spot center (cp) at the initial sequence ranking (p) to all spot centers at neighboring ranks thereof, as $Dt(p)=\Sigma_r Dw(p,r)$, calculate a cost (C,1(p, r)) of a local permutations $\pi(p)=q$ as, $C,1(p, r)=Dt(q)-Dt(p)$, calculate a first total cost $Ct,1(\pi)=\Sigma_p C,1(p, r)$, of the first total permutation (u=1), The TPS may define all possible second, third and successive total permutations (u=2, 3, 4, . . . ) of the initial sequence ranking for the chosen ranking jump (h), which are different from each other and from the first total permutation (u=1). For each of the second, third; and successive total permutations defined in the preceding step, a corresponding second, third, and successive total costs are calculated, $Ct,u(\pi)=\Sigma_p C,u(p, r)$. The final step may include selecting the total permutation (u=1, 2, 3, . . . ) yielding the lowest total cost (Ct,u($\pi$)). This method may require more computational power than the previous local optimization method discussed supra but is more effective in defining a sequence yielding a high fraction of Vs wherein DRa≥DRa0.

Selection of the Beam Scanning Sequence—Scarf Method

Ultra-high dose rate (HDR) irradiation can be performed on small fields by PBS using particle therapy systems currently available on the market. For example, the Proteus Plus system of IBA can deliver HDR plans for fields of width, W=3.2 cm and lengths, L>40 cm. This performance can be taken advantage of in yet an alternative method for selecting a beam scanning sequence yielding DRa≥DRa0 for at least the predefined fraction of each selected volume (Vs), referred to as the scarf method. As mentioned supra, each specific volume (Vs) is comprised within a specific peripheral surface and the sequence optimization for each specific volume (Vs) may be initiated with steps to define a specific volume outline (V0) formed by a projection parallel to the beam direction onto the surface plane (P0), and define a sub-set of the spot position pattern (x, y) intersecting or included within the specific volume outline (V0).

A scarf sequence unit cell may be defined with the steps to, as illustrated in FIG. 7, define an initial spot (S0v1) for being irradiated first by a first beamlet, define successive second, third, to $w^{th}$ spots, each sequentially adjacent to one another and all aligned along a width direction, define a $(w+1)^{th}$ spot (S0v(w+1)) as being adjacent to the $w^{th}$ spot (S0vw) along a length direction, different from, and in some embodiments normal to the width direction, define $(w+_2)^{nd}$ to $2w^{th}$ spots each sequentially adjacent to one another and all aligned along the width direction, define a $(2w+1)^{th}$ spot (S0v(2w+1)) as being adjacent to the $2w^{th}$ spot (S02vw) along the length direction.

The steps for defining the scarf sequence unit cell are repeated N times, from an $(Aw+1)^t h$ spot (S0v(Aw+1)) until a $((A+2)w+1)^{th}$ spot (S0v((A+2)w+1), with A=2 to 2N, forming a first scarf of width (W) equal to a distance separating the first from the $w^{th}$ spots, and of length (L) equal to the distance separating the first from the $(2N+1)^{th}$ spots. The width (W) of the scarf may be limited by the constraint that the mean dose deposition rate (DRa) of the $2w^{th}$ spot, which is adjacent to the first spot, is superior or equal to the predefined value (DRa0) (i.e., DRa(S0v(2w))≥DRa0).

The scarf method may allow the application of HDR irradiation over a stripe (="scarf") of substantially unlimited length (L), but strongly limited in the width thereof, by the latter constraint. For a particle therapy system capable in a time (ti) of depositing a dose (D) to any one spot (S0vm) at a given dose rate (DR) followed by moving from that spot to an adjacent spot following a scarf sequence unit cell can have a maximum width W=(w−1)di, such that >1 D1i/(2w−1)ti≥DRa0, wherein di is a distance separating two adjacent spots, (w−1) is the number of intervals between the first and $w^{th}$ spots which are spots located on opposite edges of the scarf along a same line, and D1i is a dose deposited onto the first spot by a beamlet (i) centered on any one of the first 2w spots in the sequence forming the scarf sequence unit cell which is composed of 2 lines.

In case a specific volume outline (V0) has a width larger than the width (W) of a scarf, the scanning sequence optimization may further include defining a second and optionally a sequence of third and successive scarves, each parallel to the first scarf, and each adjacent to or slightly impinging with the preceding scarves in the sequence of first, second and successive scarves, as illustrated in FIG. 7. This method is advantageous in that it may cover an area of substantially unlimited length (L), as discussed supra, but also of substantially unlimited width (W). One drawback, however, is that there is a stripe, represented as a shaded area in FIG. 7, at the intersection between two adjacent scarves, which cannot be irradiated at the required DRa, as the time required for irradiating a $w^{th}$ spot (S0vw) of the first scarf and an adjacent first spot (S0v1) of the second scarf is too long to maintain an irradiation at the required DRa in the area wherein adjacent spots of the first and second scarves impinge into one another. There therefore may be a risk that cells located within the shaded stripe in FIG. 7 are irradiated at CDR, and not at HDR (i.e., at the required DRa). If the stripe encloses healthy cells, and the deposited doses are high enough to kill the cells, this stripe may be considered as sacrificial. Depending on the geometry of the tumoral region and on the type of tumour and healthy cells, a clinician may decide whether a sacrificial stripe is agreeable and may decide to locate it such as to affect the least possible healthy cells. Note that the scarf needs not be in the shape of a rectangle as illustrated in FIG. 7 in case the spot position pattern (x, y) is not aligned along two straight directions normal to one another. Alternatively, the clinician may use a different method for selecting a beam scanning sequence yielding DRa≥DRa0 for at least the predefined fraction of each selected volume (Vs).

The scarf method may be implemented to other patterns than scarves, such as a spiral pattern.

Single Beam vs Multiple Beam TPS

The TPS described supra include a single beam composed of several beamlets parallel to a first beam direction. In case the TPS does not succeed in defining a beamlet sequence ensuring that at least the predefined fraction of Vs is irradiated at a mean dose deposition rate (DRa) superior or equal to the predefined value (DRa0) (i.e., DRa≥DRa0), a multi-beam treatment plan can be implemented instead.

Figure 4C:
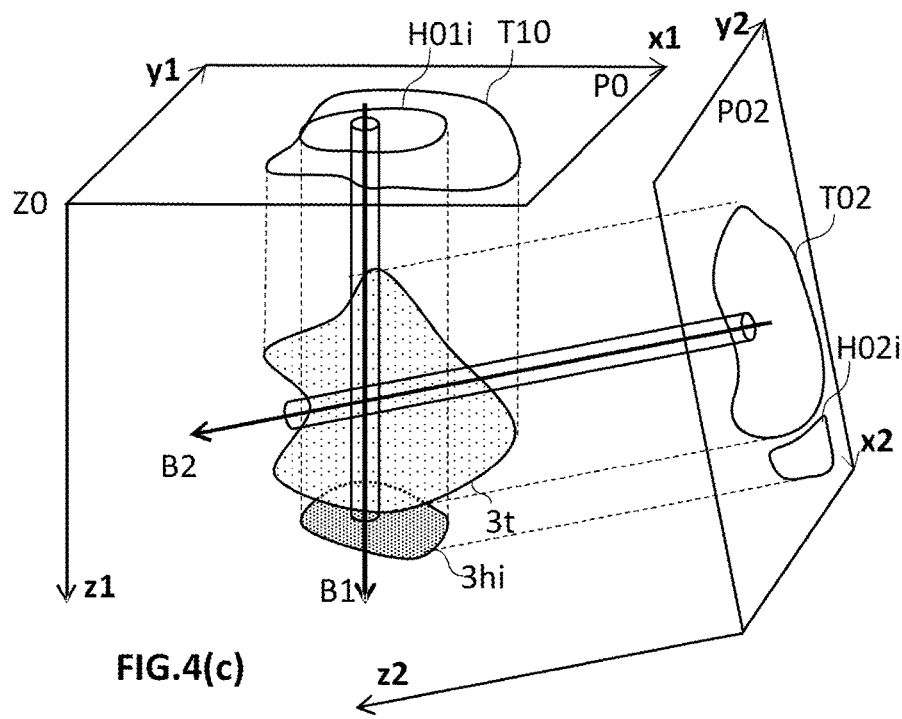
FIG. 4(c) shows the same target tissue as in FIG. 4(a) but treated with two beams propagating along different orientations (z1, z2) and crossing within the peripheral surface.

As illustrated in FIG. 4(c), a multi-beam treatment plan uses two or more beams, each composed of several beamlets and each parallel to different beam directions (z1, z2), all secant to one another. The beamlets scanning sequence stage may be repeated with additional beams until at least the predefined fraction of spots is irradiated at DRa≥DRa0. As can be seen in FIG. 4(c), using more than one beam allows a larger dose to be deposited into the target (3t) where two beams cross each other. By ensuring that the treatment plan avoids two beams from crossing each other outside the peripheral surface, it may be ensured that lower doses are deposited onto healthy cells, which are crossed by one beam only. Furthermore, as healthy cells are crossed by one beam only, the dose rate constraints (DRa≥DRa0) are considered for each beam independently. Using several beams may extend the duration of a treatment fraction j. Again, this is a choice that may be made by the clinician.

Pre-Optimizer Module

The TPS of the present disclosure may be implemented to existing "conventional TPS" by including a pre-optimizer module separate from and interacting with the conventional TPS. The pre-optimizer module may be configured for determining the beamlets scanning sequence stage only. In an embodiment, however, the beam definition stage, the dose rate definition stage, and the beamlets scanning sequence stage may be determined by the pre-optimizer module. The pre-optimizer module takes into account the performance of the particle therapy system used for later implementing the TPS to establish for a given spot position pattern (x, y) determined by the beam definition stage, the number, dimensions, and geometries of the selected volumes (Vs) defined by the beamlets scanning sequence stage, which may reasonably be irradiated at HDR by the particle therapy system with the dose rates defined by the dose rate definition stage, ensuring that DRa≥DRa0 at least in the predefined fraction of Vs.

Once the pre-optimized module has established that it is possible with a given particle therapy system to irradiate the specific volumes (Vs) such that DRa≥DRa0 in at least the predefined fraction of Vs, the parameters determined by the pre-optimized module may be introduced into the conventional TPS for establishing and defining the dose definition stage. This may be very advantageous when using existing particle therapy systems and existing conventional TPS, which were not designed to implement the properties of the FLASH effect. The pre-optimized module allows setting the bases for a realistically implementable TPS with irradiation of the predefined fraction of Vs at HDR (i.e., DRa≥DRa0), and steps of defining the doses to be deposited within the target tissue (3t) is to be defined by the dose definition stage carried out by the conventional TPS. The definition of the treatment plan may be an iterative process, wherein the results of a former run are used as starting parameters for a next run, until an agreeable treatment plan is obtained.

Equivalent Healthy Fraction Dose (Dmhij)

The FLASH effect was identified on the basis of observations that tumoral cells are killed similarly, independently of the dose deposition rate (DR), and a predefined Normal Tissue Complication Probability (NTCP0i) of a healthy tissue (3hi) not to be exceeded is reached at lower doses deposited at conventional dose deposition rates (CDR) than it is at ultra-high dose deposition rates (HDR), as shown in FIGS. 4(a) to 4(c).

In other words, the corresponding healthy dose (Dhij) deposited onto a healthy tissue required for reaching a given Normal Tissue Complication Probability (=NTCP) depends strongly on the dose deposition rate (DR) at which the dose was deposited. This is illustrated graphically in FIGS. 2(a) and 2(b). Note that the expression "healthy dose" is used herein as a contraction of "dose delivered to a healthy cell," and is not to be understood as a dose which is beneficial to the health of a cell. By contrast, this does not seem to be the case for tumoral cells which dose required for reaching the given NTCP is not dependent on the dose deposition rate, which means that the graph of FIG. 2(a) applied to tumoral cells instead of healthy cells would show substantially straight, vertical NTCP lines (not shown), instead of the S-shaped curves illustrated in FIG. 2(b).

FIG. 2(a) shows iso-NTCP lines in a plot of the dose deposition rate (DR) as a function of healthy dose (Dhij) for values of NTPC comprised between 10% and 100% probability. Assuming a value NTCP0i of the NTCP not to be exceeded during a fraction j of the treatment is 50% probability of complication, then doses left of the iso-NTCP line labelled (0.5) represented by a shaded area can be deposited at corresponding dose deposition rates. It can be seen that the dose (D) defining the iso-NTCP line=50% strongly depends on the rate at which the dose is being deposited.

FIG. 2(b) is a direct consequence of FIG. 2(a), wherein the white dots aligned at the ordinate DR=1 Gy/s of FIG. 2(a) are reported in FIG. 2(b) showing the doses (Dhij) required for reaching a given NTCP at said dose rate, yielding a sigmoid curve of white dots. The same exercise was repeated with the black dots aligned at the ordinate DR=103 Gy/s of FIG. 2(a) which are reported in FIG. 2(b) yielding the sigmoid curve of black dots. Taking NTCP0i=50% as in FIG. 2(a), yields a corresponding shaded area indicative of the doses which can be deposited onto healthy cells of a healthy tissue (3hi) at these two deposition rates.

An equivalent healthy fraction dose (Dmhij) can be defined as a sum Dmhij=(Dchij+α Dhhij) of a conventional healthy fraction dose (Dchij) and a product of an equivalence coefficient (α) and of a high rate healthy fraction dose (Dhhij), with α≤1, or in some embodiments α>0.5.

Figure 2C:
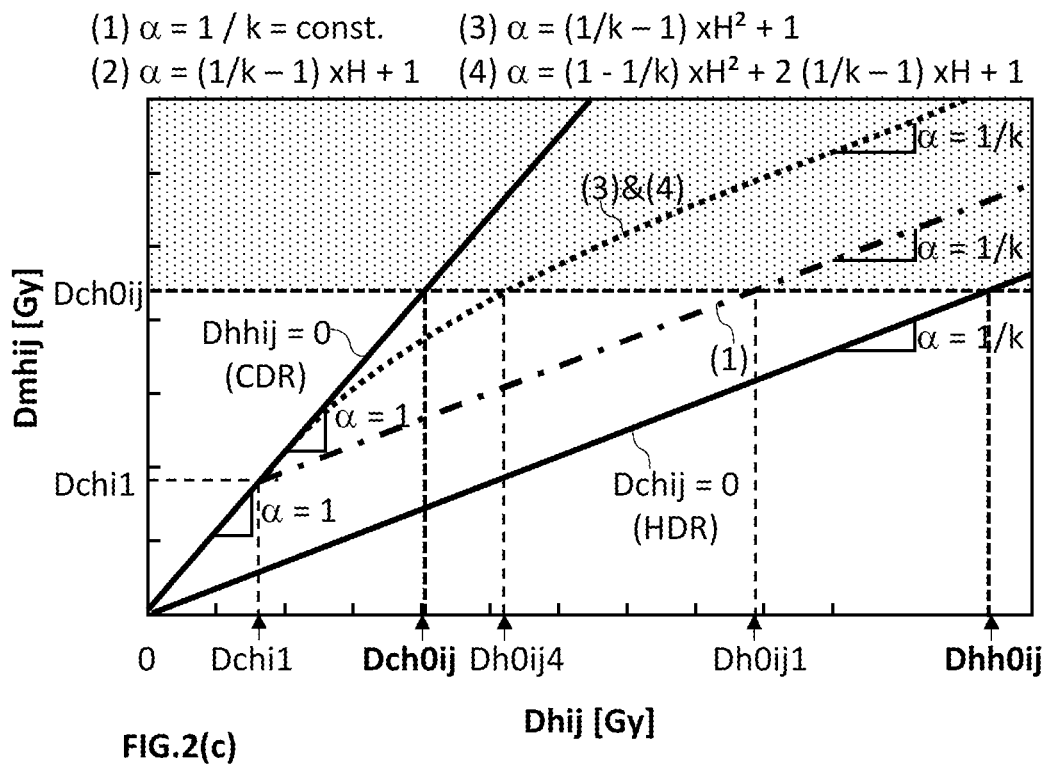
FIG. 2(c) shows the relationship of Dmhij as a function of Dhij for different values of the equivalence coefficient ($\alpha$).

The equivalent healthy fraction dose (Dmhij) may be an equivalent dose applied at least partly at HDR and yielding a same or lower probability of complication of a healthy cell (3hi) (NTCP0i) as if the healthy fraction dose (Dhij) had been deposited onto the healthy cell at a conventional dose deposition rate (CDR) only. As can be seen in FIGS. 2(a) to 2(c) the equivalent healthy fraction dose (Dmhij) is comprised between the conventional healthy fraction dose (Dchij) deposited at CDR only and the high-dose healthy fraction dose (Dhhij) deposited at HDR only, depending on a HDR proportion, xH=Dhhij/(Dchij+Dhhij), of doses deposited at ultra-high rate.

The healthy cells may be spared by fulfilling criteria that the healthy fraction dose (Dhij) received at each fraction j does not exceed a predefined threshold for preserving the healthy cells at the end of the fraction j, and the total healthy doses (DhTi) received and cumulated at the end of the N fractions does not exceed a predefined threshold for preserving the healthy cells at the end of the treatment of N fractions.

Considering the equivalent healthy fraction dose (Dmhij) as defined supra, condition (C2.1) can be fulfilled by ensuring that the equivalent healthy fraction dose, Dmhij=Dchij+α Dhhij≤Dch0ij, wherein Dch0ij is the maximum conventional healthy fraction dose not to be exceeded during a fraction to preserve the healthy cells. The second criterion (C2.2) can be fulfilled by ensuring that an equivalent healthy dose, DmhTi=Σ Dmhij=Σ (Dchij+α Dhhij)≥DchT0i, wherein DchT0i is a maximum conventional healthy dose cumulated over the N fractions j not to be exceeded to preserve the healthy cell.

The value of the equivalence coefficient α can be determined for dose depositions at ultra-high dose deposition rates (HDR) by establishing NTCP curves as a function of dose (Dhij) and dose deposition rate (DR) as illustrated for example in FIGS. 2(a) and 2(b). At sufficiently high dose deposition rates, wherein the dose (Dhh0ij) yielding a predefined NTCP0i becomes independent of the dose rate the factor α becomes substantially constant (i.e., the right-hand vertical portion of the solid curves in FIG. 2(a)), and may be defined as being equal to 1/k, wherein k=1.2 to 1.5 (i.e., α=1/k, with k=1.2 to 1.5), or in some embodiments, α<0.9, α<0.85, or α<0.7.

FIG. 2(c) illustrates various examples of the relationship between the equivalent healthy fraction dose (Dmhij) and the healthy fraction dose (Dhij). The solid lines show the relationship for deposition at CDR only, labelled "Dhhij=0 (CDR)", and at HDR only, labelled "Dchij=0 (HDR)". Considering that Dmhij=Dchij+α Dhhij, and that Dhij=Dchij+Dhhij, it follows that, at CDR only, Dhhij=0 and therefore Dmhij=Dhij, defining the straight line of slope 1 labelled "Dhhij=0 (CDR)" of FIG. 5(a), which intercepts the horizontal dashed line Dmhij=Dch0ij not to be exceeded to preserve the healthy tissues (3hi) at a value of Dhij=Dch0ij, and at HDR only, Dchij=0 and therefore Dmhij=α Dhhij, defining the straight line of slope α=1/k labelled "Dchij=0 (HDR)" of FIG. 5(a), which intercepts the horizontal dashed line Dmhij=Dch0ij not to be exceeded to preserve the healthy tissues (3hi) at a value of Dhij=Dhh0ij.

The doted and mixed lines are examples of irradiation comprising dose depositions at both CDR and HDR, expressed in terms of xH=Dhhij/(Dchij+Dhhij) for different values of a as indicated in FIG. 2(c).

Determination of DRa0

The mean ultra-high dose deposition rate boundary (DRa0) to be reached for sparing healthy cells present in specific volumes (Vs) by FLASH effect can be determined using the equivalent healthy fraction dose (Dmhij) described supra. For example, using NTCP curves as illustrated in FIG. 2(a) for a given healthy tissue (3hi) and fixing a value of the predefined probability of complication (NTCP0i), (e.g., NTCP0i=50% —this value can be defined by a clinician), the minimum value of the mean ultra-high dose deposition rate boundary (DRa0) required for depositing a given dose within the predefined value of NTCP0i, by reading the value of the dose deposition rate (DR) on the ordinate of FIG. 2(a), corresponding to the intersection point between the NTCP0i curve and the value of the given dose in the abscissa of FIG. 2(a). Once a value of DRa0 is set, the various stages of the treatment planning can be run to establish a treatment plan. If the required mean ultra-high dose deposition rate boundary (DRa0) is too high to ensure that at least the predefined fraction of the specific volumes be irradiated at a mean dose deposition rate, DRa≥DRa0, then the exercise can be repeated with lower dose values or, as described supra, by using more than one beam of different beam directions.

The TPS of the present disclosure takes for the first time in consideration the mean dose deposition rate (DRa) as a determining parameter for obtaining or not a FLASH effect. It also takes into consideration the performance of the particle therapy system used for the treatment. This issue arises with irradiation of a target by PBS, which involves sequentially depositing doses to a specific sub-volume, then to a second specific volume, and so on until the whole volume of the target is irradiated. PBS can be a discrete PBS, wherein a beamlet irradiates the target tissue along a trajectory centered on a first spot. Then the beamlet is interrupted for the time required for moving the beamlet from the first spot in the sequence to the second spot in the sequence, and thence the beamlet is activated again to irradiate the target tissue along a trajectory centered on the second spot. Alternatively, the PBS may be a continuous PBS, wherein the beamlet is not interrupted during the translation from a first spot to a second spot in the sequence. For example, the scarf method is suitable for implementing both discrete and continuous PBS.

Since a beamlet centered on a given sub-volume also deposits doses on neighboring sub-volumes, the problem of the mean dose deposition rate (DRa) may become acute, since the value thereof takes into account the total time (Δt) required to deposit the total dose by all neighboring beamlets leaking into the given sub-volume.

With the beamlets scanning sequence stage, the TPS of the present disclosure ensures that at least a predefined fraction of the specific volumes (Vs) may be irradiated by PBS at a mean dose deposition rate, DRa≥DRa0. This way, the FLASH effect may be effectively used to spare a substantial number of healthy cells, while killing the tumoral cells contained within the peripheral surface.

The following abbreviations are intended to have the meanings described below:

| REF | DESCRIPTION |
| --- | --- |
| 3hi | Healthy tissue i |
| 3t | Target tissue |
| 3z | Uncertain zone |
| B, B1, B2, Bm | particle beam |
| CDR | conventional dose deposition rate |
| D | Dose |
| d | Spot diameter |
| Dch0ij | Maximum conventional healthy fraction dose |
| DchT0i | Maximum conventional healthy dose cumulated over the N fractions j |
| Dchij | Conventional healthy fraction dose |
| DctT | Conventional target dose |
| Dctj | Conventional target fraction dose |
| Dhhij | High rate healthy fraction dose |

-continued

| REF | DESCRIPTION |
|---|---|
| DhhOij | maximum high rate healthy fraction dose |
| Dhij | $Dhij = Dchij + Dhhij$ is the healthy fraction dose |
| DhTi | $DhTi = \Sigma\,Dhij = \Sigma\,(Dchij + Dhhij)$ is the total healthy dose cumulated over the N fractions j |
| Dj | Dose deposited at one point by a beamlet j |
| Dmhij | $Dmhij = Dchij + \alpha\,Dhhij$ is the equivalent healthy fraction dose |
| DmhTi | $DmhTi = \Sigma\,Dmhij = \Sigma\,(Dchij + \alpha\,Dhhij)$ is the total equivalent healthy dose cumulated over the N fractions j |
| Dmtj | $Dmtj = Dctj + Dhtj$ is the target fraction dose |
| DmtT | $DmtT = DctT + DhtT$ is the Total target dose |
| DmtT0 | Minimum target dose |
| DR | Dose deposition rate (or deposition rate) |
| DRa | Mean deposition rate |
| DRa0 | Mean ultra-high dose deposition rate boundary |
| DR1-DRk | Dose deposition rates deposited by one beamlet at a given point |
| H0i | Healthy tissue outline projected onto P0 parallel to z |
| HDR | Ultra-high dose deposition rate |
| k | CDR/HDR proportionality factor at ultra-high dose deposition rates, ($k = 1/\alpha$) |
| L | Length of scarf |
| NTCP | Normal Tissue Complication Probabiliy |
| NTCP0i | Maximum NTCP value for a healthy tissue (3hi) |
| P0 | Surface plane normal to the beam direction at level of skin |
| P2-Pn | Inner planes normal to the beam direction |
| PBS | Pencil beam scanning |
| S0m | Spots at plane P0 defined in spot position pattern (x, y) |
| S0vm | Spots at plane P0 defined in the sub-set of spot position pattern (x, y) |
| SOBP | Sum of Bragg Peaks |
| T0 | Target tissue outline projected onto P0 parallel to z |
| V0 | Specific volume outline projected onto P0 parallel to z |
| V1-Vn | Intersection of specific volume (Vs) with a plane P1-Pn |
| Vs | Specific volume |
| W | Width of scarf |
| W | Number of spots in a scarf width |
| x, y | Vectors defining plane normal to beam at depth (z) |
| xH | HDR-proportion = $Dhhij/(Dchij + Dhhij)$ |
| z, z1, z2 | Penetration depth and beam direction |
| z0 | $Z = 0$ (skin) |
| Z2-Zn | depth of the inner planes P2-Pn along z |
| $\alpha$ | Equivalence coefficient ($Dmhij = Dchij + \alpha\,Dhhij$) |
| $\Delta t$ | Total time of dose deposition at one point by successive beamlets. |

The invention claimed is:

1. A method of treatment with charged particles beams applied by pencil beam scanning (PBS) onto a target tissue comprising tumoral cells enclosed within a peripheral surface, which is surrounded by healthy cells, wherein the healthy cells form healthy tissues, the method comprising:
determining a total target dose to be deposited into all tumoral cells of the target tissue, which is equal to a sum of target fraction doses received at each of N fractions of irradiation, the total target dose being at least equal to a minimum target dose for killing the tumoral cells;
determining a total healthy dose equal to a sum of healthy fraction doses received by healthy cells at each fraction, such that a healthy fraction dose received at each fraction does not exceed a predefined fraction dose threshold for preserving the healthy cells at the end of the fraction, and the total healthy dose received by healthy cells does not exceed a predefined total dose threshold for preserving the healthy cells at the end of the treatment of N fractions,
a dose definition stage defining the doses to be deposited within the peripheral surface based on the total target dose;
a beam definition stage defining positions and dimensions of beamlets of the PBS during at least one high rate fraction, the beams definition stage comprising:
defining a diameter of a spot formed on a surface plane by a beamlet propagating along a beamlet axis substantially parallel to a beam direction and intersecting substantially perpendicularly the surface plane at a spot center, wherein the surface plane contacts the skin of the patient at least at the spot center,
defining a spot position pattern on the surface plane of the spots formed by different beamlets substantially parallel to the beam direction such that the spots positions pattern ensures that the spots cover a whole area defined within a projection parallel to the beam direction of the peripheral surface onto the surface plane,
a dose rate definition stage comprising defining the at least one high rate fraction, wherein specific volumes bounded by a specific volume surface enclosing healthy cells are irradiated at an ultra-high dose deposition rate greater than 1 Gy/s;
a beamlets scanning sequence stage defining a scanning sequence of irradiation of the beamlets, the beamlets scanning sequence stage comprising:
optimizing a time sequence of beamlets emission according to the spot positions pattern such that at the end of a fraction, a dose is deposited onto at least 50% of each specific volume at a mean deposition rate greater than or equal to a predefined value of a mean ultra-high dose deposition rate boundary based on the healthy fraction dose and the total healthy dose,
wherein the mean deposition rate is defined as a sum of a percentile of doses deposited by one or more beamlets onto a given volume divided by a time between the first and last doses deposited onto the given volume, the mean deposition rate being greater than or equal to 1 Gy/s, and the percentile being at least 95%.

2. The method of claim 1, wherein the beam definition stage further comprises:
defining a surface target outline and surface healthy outlines formed by a projection onto the surface plane, parallel to the beam direction, of the peripheral surface of the target tissue, and peripheral surfaces of the healthy tissues surrounding the target tissue, and
determining the spot diameter and spot positions pattern on the surface plane to homogeneously cover an area enclosed within the surface target outline.

3. The method of claim 2, wherein beam axes of two adjacent proton beamlets distributed according to the spot positions pattern are separated from one another by a distance between 1.2 and 2.5 times $\sigma$, wherein $\sigma^2$ is the variance of a Gaussian dose distribution in the spots on the surface plane formed by the two adjacent proton beamlets.

4. The method of claim 2, wherein
a first specific volume extends along a distance measured along the beam direction from the surface plane; and
the beamlets scanning sequence stage further comprises:
defining n inner planes parallel to the surface plane and distributed at corresponding depths between a depth Z1 at the level of an inner plane, and a depth Zn at a level of an $n^{th}$ inner plane, such that the specific volume is sandwiched between the first and $n^{th}$ planes,
defining specific volume projection outlines formed by a projection onto the respective surface planes parallel to the beam direction of the corresponding specific volume surface, and selecting a beamlet scanning sequence yielding for at least 50% of a selected volume defined within a cylinder of base formed by the specific volume projection outline and of height of a distance between the depth Z1 and the depth Zn, a mean dose deposition rate Dra≥Dra0, and repeating the beamlets scanning sequence stage for each specific volume different from the first specific volume.

5. The method of claim 1, wherein the specific volumes are defined as at least one of:
    cells located on either side of a portion of the peripheral surface most remote from the surface plane and crossed by the beams of the PBS to exit the target tissue,
    as a zone comprising both tumoral and healthy cells intermixed at different ratios, or
    containing healthy cells of a healthy tissue which are intersected by one or more beamlets.

6. The method of claim 1, wherein
    each specific volume is comprised within a specific peripheral surface; and
    the beamlets scanning sequence stage for each specific volume further comprises repeating, for a plurality of spots of the sub-set of the spots position pattern:
        defining a specific volume outline formed by a projection parallel to the beam direction of the specific peripheral surface of the specific volume onto the surface plane,
        defining a sub-set of the spot position pattern comprising spots intersecting or included with in the specific volume outline,
        delivering a dose to a first spot center crossed by a first beamlet,
        recording the doses delivered by the first beamlet to neighboring spot centers,
        selecting a second spot center to be irradiated directly after the first spot center based on at least one of minimizing a sum, across all spots, of the square of a difference of average dose rate and target average dose rate, maximizing an average of the average dose rates over all measured spots, or maximizing the average dose rates of each spot.

7. The method of claim 1, wherein
    each specific volume is comprised within a specific peripheral surface; and
    the beamlets scanning sequence stage for each specific volume further comprises:
        defining a specific volume outline formed by a projection parallel to the beam direction of the specific peripheral surface of the specific volume onto the surface plane,
        defining a sub-set of the spot position pattern intersecting or included within the specific volume outline,
        for each position of the spot centers of the sub-set, assigning an initial sequence ranking in the beam scanning sequence,
        defining a value for a maximum ranking jump a spot center can make in one permutation;
        defining a first total permutation of the initial sequence ranking of the spot centers composed of M local permutations based on an initial ranking of a given spot center in the initial sequence ranking and a final ranking after the permutation, with a condition of maximum ranking jump, wherein the total permutation comprises a plurality of permutations applied sequentially to the initial sequence,
        defining a weighted neighbor ranking distance of a spot center at a starting sequence ranking by:
            defining a weighted neighbor ranking distance between the spot center at the initial sequence ranking and a spot center at a neighboring sequence ranking,
            defining a total weighted neighbor distance from the spot center at the initial sequence ranking to all spot centers at neighboring ranks thereof,
        calculating a cost of a local permutations,
        calculating a first total cost of the first total permutation,
        defining a plurality of successive total permutations of the initial sequence ranking for the chosen ranking jump, each successive total permutations being different from other successive total permutations and from the first total permutation,
        calculating a total cost correspond to each of the plurality of successive total permutations, and
        selecting a total permutation yielding a lowest total cost.

8. The method of claim 1, wherein
    each specific volume is comprised within a specific peripheral surface; and
    the beamlets scanning sequence stage for each specific volume further comprises:
        defining a specific volume outline formed by a projection parallel to the beam direction of the specific peripheral surface of the specific volume onto the surface plane,
        defining a sub-set of the spot position pattern comprising spots intersecting or included within the specific volume outline,
        defining a scarf sequence unit cell by:
            defining an initial spot for being irradiated first by a first beamlet,
            defining plurality of w spots, each sequentially adjacent to one another and all aligned along a width direction,
            defining a (w+1) spot as being adjacent to the w spot along a length direction, different from the width direction,
            defining (w+2) to 2w spots each sequentially adjacent to one another and all aligned along the width direction,
            defining a (2w+1) spot as being adjacent to the 2w spot along the length direction,
        repeating the defining the scarf sequence unit cell N times, from an (Aw+1) spot until a ((A+2)w+1) spot, wherein A is comprised between 1 and (N+2), to form a first scarf of width equal to a distance separating the first from the w spot, and of length equal to the distance separating the first from the ((N+4)w+1) spot, and wherein the width of the scarf is limited by a constraint that the mean dose deposition rate of the 2w spot is greater than or equal to the predefined value.

9. The method of claim 8, wherein
    each specific volume has a width larger than the width of the first scarf, and the beamlets scanning sequence stage further comprises:
        defining a plurality of scarves, each parallel to the first scarf, and each adjacent to the preceding scarves in a sequence of scarves.

10. The method of claim 1, wherein
the beam definition stage, the dose rate definition stage, and the beamlets scanning sequence stage are determined by a pre-optimizer module separate from, a system determining the dose definition stage.

11. The method of claim 1, wherein the dose rate definition stage further defines a highest dose rate at which a given dose can be delivered by a beamlet based on a product of a maximum intensity a nozzle of a proton accelerator and function relating a proton fluence to an incident energy of the proton beam.

12. The method of claim 1, further comprising:
determining single-beam treatment plan using a single beam composed of several beamlets parallel to a first beam direction, and
in response to the predefined fraction of the specific volume being irradiated with a mean dose deposition rate greater than or equal to the predefined value, determining a multi-beam treatment plan is determined using two beams or more beams, each composed of several beamlets and each parallel to different beam directions, all secant to one another, until at least the predefined fraction of spots is irradiated at greater than the predefined value.

13. The method of claim 1, wherein the dose definition stage further comprises defining an energy shaping device for defining beamlets having an optimized Sum of Bragg Peaks (SOBP) along the penetration depth for each spot of the spot position pattern.

* * * * *